(12) United States Patent
Kobayashi et al.

(10) Patent No.: US 12,070,519 B2
(45) Date of Patent: Aug. 27, 2024

(54) COMPOSITE COMPOSITION

(71) Applicants: KIT CO. LTD., Osaka (JP); BOSQUET SILICON CORP., Osaka (JP)

(72) Inventors: Hikaru Kobayashi, Kyoto (JP); Yuki Kobayashi, Kyoto (JP)

(73) Assignees: KIT CO. LTD, Osaka (JP); BOSQUET SILICON CORP., Osaka (JP)

( * ) Notice: Subject to any disclaimer, the term of this patent is extended or adjusted under 35 U.S.C. 154(b) by 845 days.

(21) Appl. No.: 17/051,370

(22) PCT Filed: Mar. 29, 2019

(86) PCT No.: PCT/JP2019/014285
§ 371 (c)(1),
(2) Date: Oct. 28, 2020

(87) PCT Pub. No.: WO2019/211960
PCT Pub. Date: Nov. 7, 2019

(65) Prior Publication Data
US 2021/0093579 A1    Apr. 1, 2021

(30) Foreign Application Priority Data

Apr. 29, 2018 (JP) ................. 2018-087905

(51) Int. Cl.
| | | |
|---|---|---|
| *A61K 9/51* | (2006.01) | |
| *A23K 20/28* | (2016.01) | |
| *A23K 50/80* | (2016.01) | |
| *A23L 33/16* | (2016.01) | |
| *A61K 8/25* | (2006.01) | |
| *C01B 3/06* | (2006.01) | |
| *C05G 3/00* | (2020.01) | |

(52) U.S. Cl.
CPC ............ *A61K 9/5115* (2013.01); *A23K 20/28* (2016.05); *A23K 50/80* (2016.05); *A23L 33/16* (2016.08); *A61K 8/25* (2013.01); *C01B 3/06* (2013.01); *C05G 3/00* (2013.01); *A23V 2002/00* (2013.01); *A61K 2800/621* (2013.01)

(58) Field of Classification Search
CPC ............ A23K 20/28; A23L 33/16; A61K 8/25
See application file for complete search history.

(56) References Cited

U.S. PATENT DOCUMENTS

| | | | | |
|---|---|---|---|---|
| 2009/0117161 A1* | 5/2009 | Giapis | ................ | A61K 8/0237 424/59 |
| 2010/0089759 A1* | 4/2010 | Watanabe | ............. | B01J 19/088 205/74 |
| 2010/0272650 A1* | 10/2010 | Tsukada | ............ | G01N 21/6428 257/14 |
| 2016/0079591 A1 | 3/2016 | Yang et al. | | |
| 2016/0233490 A1* | 8/2016 | Put | ....................... | H01M 4/622 |
| 2017/0177885 A1 | 6/2017 | Hardee et al. | | |
| 2018/0145316 A1* | 5/2018 | Moon | ................. | H01M 4/134 |
| 2019/0038664 A1 | 2/2019 | Kobayashi et al. | | |
| 2019/0067690 A1* | 2/2019 | Chen | ..................... | B22F 1/056 |
| 2019/0216082 A1 | 7/2019 | Kobayashi et al. | | |
| 2019/0231660 A1 | 8/2019 | Kobayashi et al. | | |

FOREIGN PATENT DOCUMENTS

| | | |
|---|---|---|
| CN | 102574359 A | 7/2012 |
| CN | 105378984 B | 7/2017 |
| EP | 2588409 B2 | 5/2013 |
| JP | 5514140 B2 | 6/2014 |
| JP | 2015-113331 A | 6/2015 |
| JP | 2016-522139 A | 7/2016 |
| JP | 2016-530189 A | 9/2016 |
| WO | 2014/172914 A1 | 10/2014 |
| WO | 2015/003996 A1 | 1/2015 |
| WO | 2017-130709 A1 | 8/2017 |
| WO | 2018/037752 A1 | 3/2018 |
| WO | 2018/037818 A1 | 3/2018 |
| WO | 2018/037819 A1 | 3/2018 |
| WO | 2012000858 A1 | 1/2021 |

OTHER PUBLICATIONS

Rahaman, O. et al. A first-principles study on the effect of oxygen content on the structural and electronic properties of silicon suboxide as anode material for lithium ion batteries Journal of Power Sources 307 (2016) 657-664 (Year: 2016).*
EPO, Extended European Search Report for European Patent Application No. 19 79 5873, Dec. 14, 2021.
China State Intellectual Property Office, Office Action for Chinese Patent Application No. 201980041485.x, Feb. 3, 2023 (a machine translation is attached hereto).
Japan Patent Office, Office Action for Japanese Patent Application No. 2020-105928, Mar. 7, 2023 (a machine translation is attached hereto).
Government of India, Hearing Notice for Indian Patent Application No. 202027050206, Mar. 30, 2023.
Taiwan Patent Office, Office Action for Taiwanese Patent Application No. 108112223, Dec. 22, 2022 (A machine translation is attached hereto).
EPO, Office Action for European Patent Application No. 19 795 873.9, Dec. 9, 2022.
Taiwan Intellectual Property Office, First Office Action for Taiwanese Patent Application No. 108112223, Jun. 1, 2022.
WIPO, International Search Report for International Application No. PCT/JP2019/014285, Jun. 25, 2019.
Fujie et al., "Hydrogen generation by the reaction of Si nanopowder with water in neutral pH region" (Proceedings of the 64th JSAP Spring Meeting, Introduction, Experiment, Results and discussion), 2017, 15a-421-6, non-official translation (Cited in International Search Report for International Application No. PCT/JP2019/014285 (Cite No. 1 of Non-Patent Literature Documents in this list) and cited in Japanese Office Action for Japanese Patent Application No. 2020-517034 (Cite No. 3 of Non-Patent Literature Documents in this list).

(Continued)

*Primary Examiner* — Andrew S Rosenthal

(57) ABSTRACT

One composite composition of the present invention contains: a silicon fine particle; and a silicon suboxide ($SiO_x$, wherein x is ½, 1, or ³⁄₂) and/or a mixed composition of the silicon suboxide and silicon dioxide, at least partially covering the surface of the silicon fine particle.

19 Claims, 5 Drawing Sheets

(56) References Cited

OTHER PUBLICATIONS

Japan Patent Office, Office Action for Japanese Patent Application No. 2020-517034A, Jun. 16, 2020 (A machine translation is attached hereto).

Matsuda et al., "Water decomposition due to silicon nanopowder and hydrogen concentrations", Extended Abstracts of the 62nd JSAP Spring Meeting, 2015, 12-031.

Intellectual Property India, Indian First Examination Report for Indian Patent Application No. 202027050206, Apr. 12, 2022.

China State Intellectual Property Office, Office Action for Chinese Patent Application No. 201980041485.x, Sep. 13, 2023 (a machine translation is attached hereto).

Australian Government IP Australia, Examination Report No. 1 for standard patent application, Jan. 17, 2024.

\* cited by examiner

[Fig. 1]
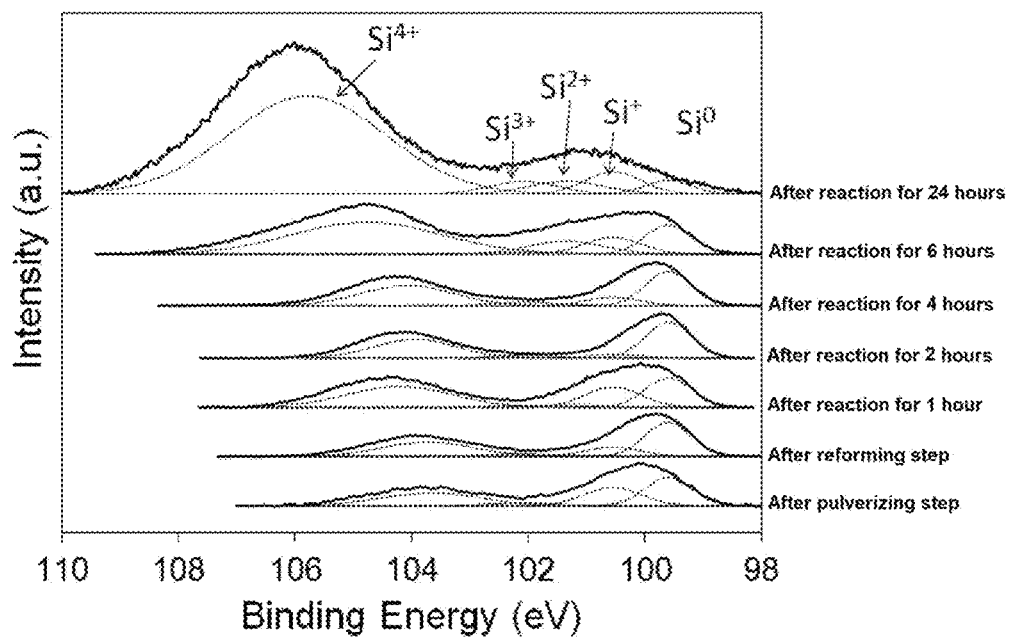
[Fig. 2]
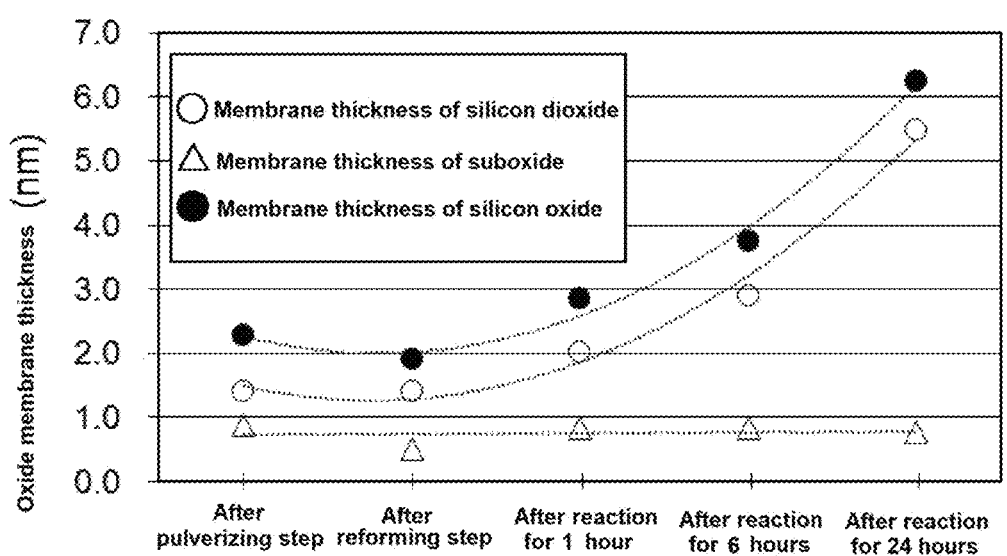

[Fig. 3]
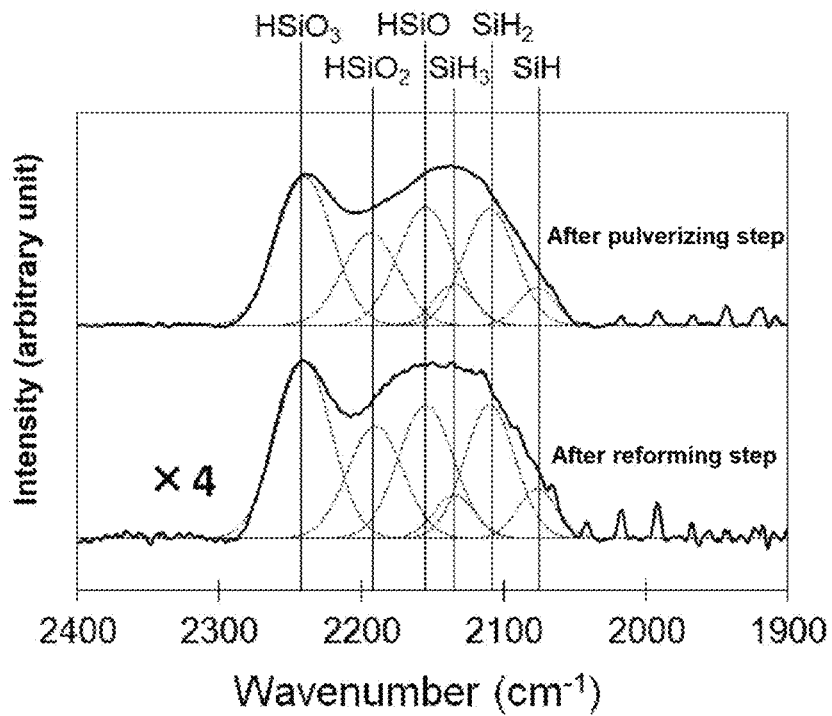
[Fig. 4]
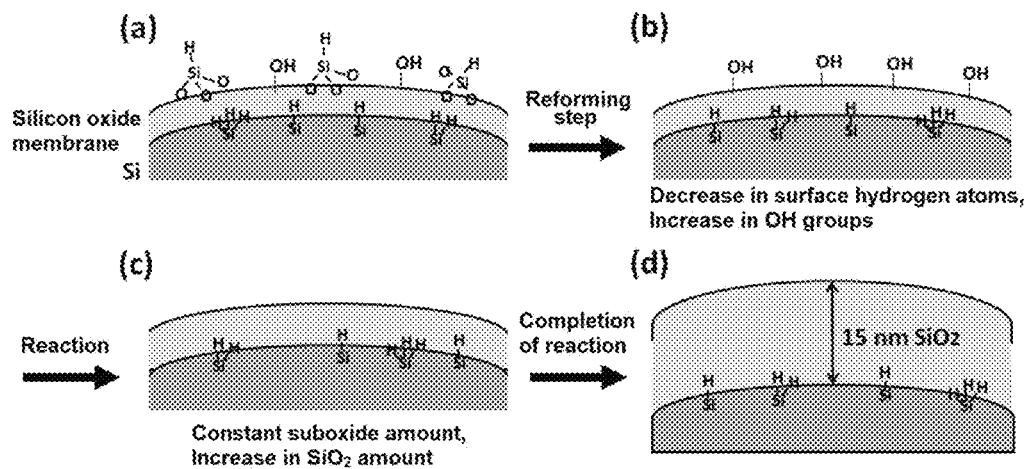

[Fig. 5]
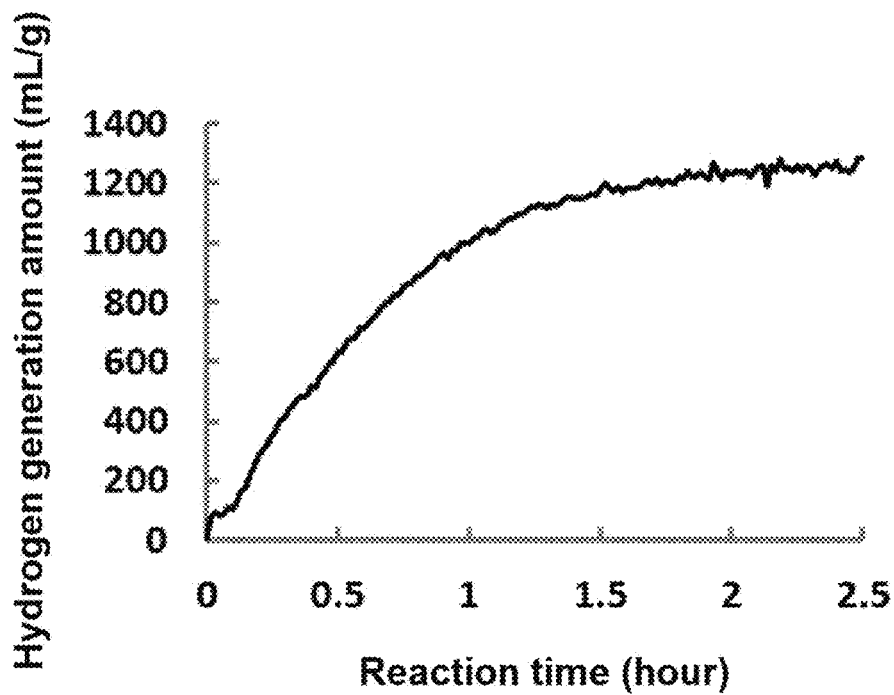
[Fig. 6]
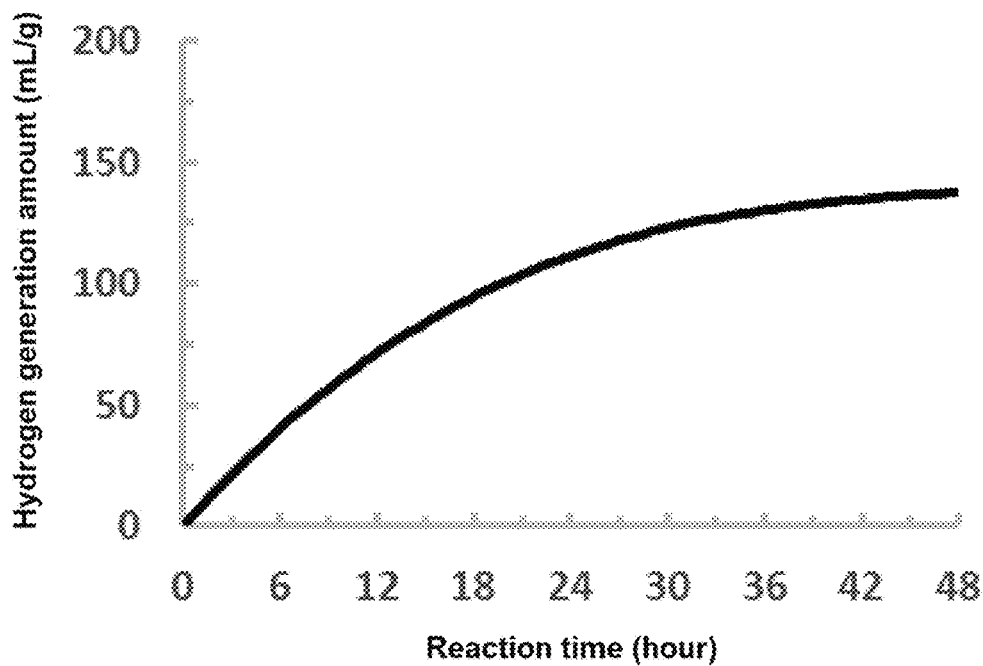

[Fig. 7]
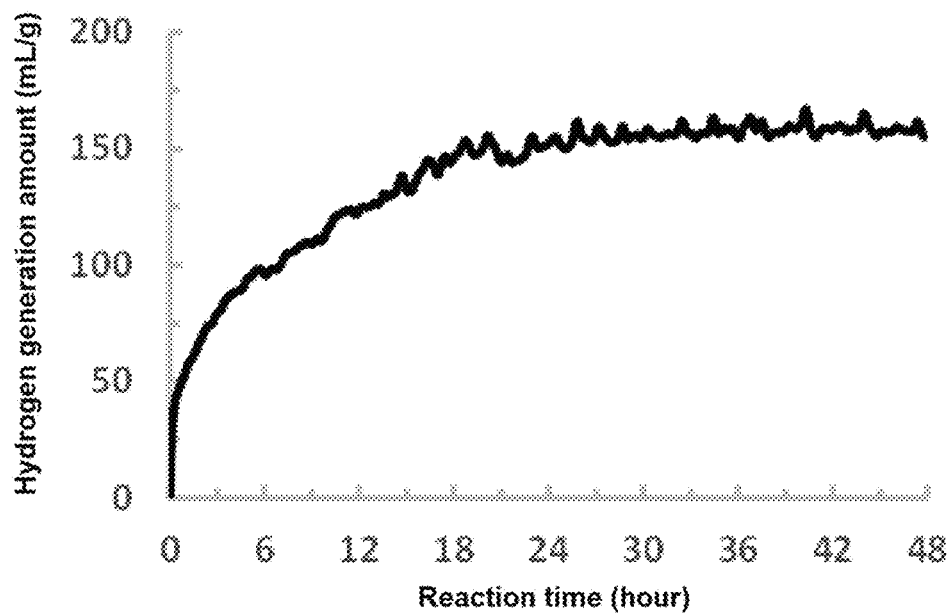
[Fig. 8]
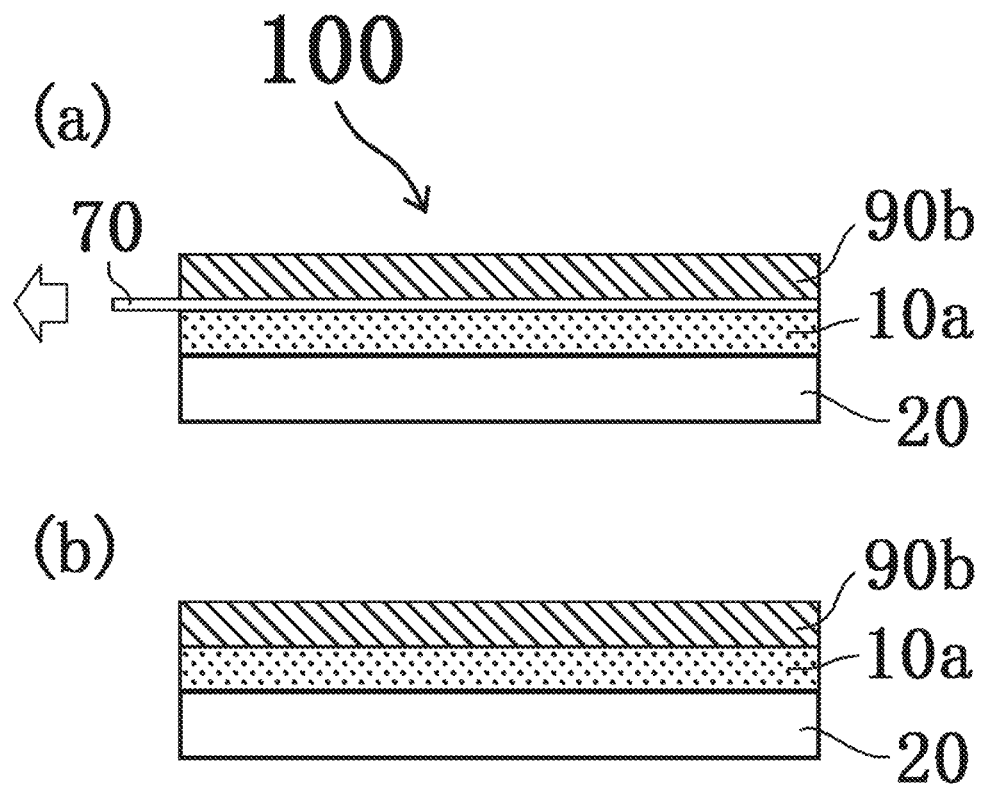

[Fig. 9]
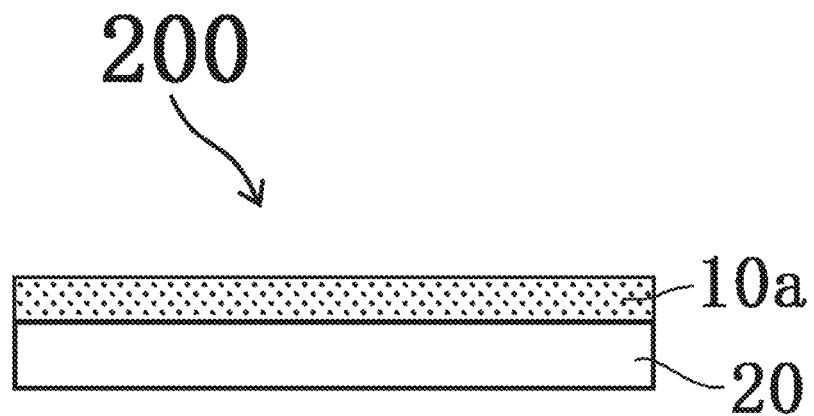

COMPOSITE COMPOSITION

TECHNICAL FIELD

The present invention relates to a composite composition, and more specifically relates to a composite composition containing silicon particles having a hydrogen generating capability and/or aggregates thereof, and a pharmaceutical product, a hydrogen supply material, a food for rearing, a supplement, a food additive, a health food, and a compound which contain the composite composition.

BACKGROUND ART

Hydrogen is widely applied, and there are also many expected uses for the hydrogen. As one example among these, announcements and the like involving subjects and growth caused by oxidative stress are found. For example, in a body of an animal such as a human, active oxygen is present, which is derived from oxygen produced in mitochondria in cells by metabolism in the body and subcutaneously under irradiation of ultraviolet rays, and taken in from the lung. The active oxygen is known to oxidize and damage cells which form a living body while it is necessary for life support. Particularly, hydroxyl radicals which have the strongest oxidizing power in the active oxygen are considered to cause various diseases such as cancer, stroke, myocardial infarction, diabetes, other lifestyle diseases, and skin disorders such as skin aging and dermatitis. Therefore, it is desirable that excess active oxygen, particularly hydroxyl radicals, which have not been used in a reaction useful for a living body, are prevented from being present in the body wherever possible.

Taking only the oxidative stress in the body, hydroxyl radicals produced in the body are eliminated by reacting with some substances. An in vivo antioxidant substance such as polyphenol, vitamin C, α-tocopherol, or glutathione is generally assumed as an example of substances which eliminate the hydroxyl radicals. However, these substances eliminate not only the hydroxyl radicals but also active oxygen such as hydrogen peroxide which has a function in the body, so that the substances may exert adverse effects (side effects) such as a decrease in immunity. Hydrogen is also known to be able to eliminate the hydroxyl radicals. However, the hydrogen reacts only with the hydroxyl radicals in the active oxygen, so that it does not exert the above-described adverse effects (side effects). Therefore, a device for producing hydrogen water containing hydrogen which eliminates hydroxyl radicals in the body has been proposed (e.g., Patent Document 1).

However, the saturated solubility of hydrogen in water at 25° C. is as extremely low as 1.6 ppm, and hydrogen in hydrogen water is easily diffused into the air. Therefore, in order to take hydrogen in the body in an amount necessary for eliminating hydroxyl radicals, it is necessary to keep the concentration of dissolved hydrogen in hydrogen water high. Therefore, in a method in which hydrogen water is ingested, it is impossible to take hydrogen in the body in an amount sufficient to react the hydrogen with hydroxyl radicals in the body. Thus, in order to easily take hydrogen in the body, a hydrogen-containing composition containing hydrogen and a surfactant has been proposed (Patent Document 2), but a hydrogen concentration cannot be kept high in the body over along time. The hydroxyl radicals have a short life, and are constantly generated in the living body, which makes it necessary to constantly supply a high concentration of hydrogen into the body in order to eliminate the hydroxyl radicals.

Based on the above-described background, the present inventors disclose an orally administrable solid preparation containing a silicon fine particle as a main component and having a high hydrogen generating capability (Patent Document 3).

PRIOR ART DOCUMENTS

Patent Documents

Patent Document 1: Japanese Patent No. 5514140
Patent Document 2: Japanese Patent Laid-Open Publication No. 2015-113331
Patent Document 3: International Publication WO2017/130709
Patent Document 4: International Publication WO2018/037752
Patent Document 5: International Publication WO2018/037818
Patent Document 6: International Publication WO2018/037819

Non-Patent Document

Non-Patent Document 1: MATSUDA et al., Water decomposition due to silicon nanopowder and hydrogen concentrations, Extended Abstracts of the 62nd JSAP Spring Meeting, 2015, 12-031.

SUMMARY OF THE INVENTION

Problems to be Solved by the Invention

However, even if hydrogen water is ingested, the amount of hydrogen contained in 1 liter of the hydrogen water at 25° C. is only 18 ml at a maximum in terms of gas. Hydrogen is the smallest molecule, is light, and has a high diffusion rate, so that the hydrogen water cannot be completely stored in a container accommodating the hydrogen water. One utilization example in a living body will be described, and much of hydrogen in the hydrogen water is gasified in the stomach. This has a problem of causing pnenmophagia (so-called "burp") since a sufficient amount of hydrogen is not taken in the body. Therefore, according to known information, it is impossible to keep the hydrogen concentration high in the stomach over a long time by ingesting hydrogen water, and to continuously ingest the hydrogen water a large number of times over a longtime. Meanwhile, when a hydrogen-containing composition with hydrogen encapsulated by a surfactant is ingested, it is impossible to ingest the hydrogen-containing composition for taking a sufficient amount of hydrogen in the body over a longtime. In addition, the above-described problem that hydrogen is released in the stomach also may occur. Furthermore, when the hydrogen water is temporarily used on the skin in a known method, the hydrogen water is used in the air, so that hydrogen is diffused into the air and scattered in a short time at a much higher hydrogen diffusion rate than that in the body, which makes it extremely difficult or impossible to absorb the hydrogen through the skin. The situation in the living body has been described here, but there are other various problems for practical use such as industrial use, plant use, or energy use.

The present invention solves at least one of the above-described technical problems, and can largely contribute to a stronger hydrogen generating capability of a silicon fine particle having a silicon suboxide, that is, generation of a large volume of hydrogen in the body or space for a long time, or more accurate drawing of the hydrogen. In order to obtain an arbitrary hydrogen generation amount depending on the use, the hydrogen generation amount can be arbitrarily adjusted depending on the amount of the composite composition used, and the size of the fine particles, and the like.

Solutions to the Problems

The present inventors found a technique of generating hydrogen at a necessary place or site without preliminarily dissolving hydrogen gas in water or the like in the previous research and development, and conducted analyses and studies in order to significantly increase a hydrogen generation amount from silicon fine particles, and to more strongly or more accurately draw the hydrogen over a longer time. Hitherto, by paying attention to an environment in which silicon fine particles are present (e.g., the pH value and the like of intestinal fluid in a living body, and the pH value of hydrogen generation which does not adversely affect a human body), devices to optimize the environment have been mainly accumulated. For example, when the silicon fine particles are used on the skin or the like, similar hydrogen generation can be realized by using a suitable pH adjusting agent in combination. In the above-described different fields such as an industrial field, a plant field, and an energy field, a hydrogen generation method, a hydrogen storage method, and a hydrogen use method, which are suitable for the use and the scene are considered. Therefore, industrially, it is extremely significant to provide a composite composition which realizes a novel, safe, and effective hydrogen generation method, and a method for using the same.

However, through repeated research and development, the present inventors found that, by focusing on the silicon fine particles themselves, more specifically, the surfaces of the silicon fine particles, the oxidation state and composition of a silicon oxide membrane covering the surfaces, the physical and chemical surface configuration states of the surface of the silicon oxide membrane, and more microscopic physical properties or characteristics at the interface between the surfaces and the silicon oxide membrane, and actively utilizing the physical properties or characteristics, a hydrogen generation amount from the silicon fine particles can be significantly increased, and a hydrogen generating capability can be more strongly or more accurately drawn over a longer time. The present inventors also found that the hydrogen generation amount required depending on the use can be arbitrarily adjusted by the method for preparing the composite composition, the amount of the composite composition used, the size of the fine particles, and the pH value, and the like.

The present inventors analyzed and studied the surfaces of silicon fine particles manufactured by performing specific chemical processing, a silicon oxide membrane covering the surfaces, and/or the interface between the surfaces and the silicon oxide membrane from various viewpoints. As a result, it was clarified that the silicon oxide membrane in a special state is formed on the silicon fine particle at the beginning of manufacturing. After further analysis, the inventors found the following points.

(1) The silicon oxide membrane contains many multiple types of oxides which are stoichiometrically different from $SiO_2$, and referred to as a "silicon suboxide".
(2) The presence of a composite composition containing a silicon particle and the silicon oxide membrane (containing a silicon suboxide and silicon dioxide).
(3) The presence of a composite composition formed by using a silicon fine particle forming the silicon particle as a nucleus and causing various silicon oxide membranes (containing a silicon suboxide and silicon dioxide) to at least partially cover the surface of the silicon fine particle.
(4) The surface of the silicon fine particle exhibits hydrophilicity; the concentration of hydrogen bonded to the surface of the silicon fine particle (the concentration of a SiH group) is low; and the surface of the silicon oxide membrane has many OH groups (that is, SiOH groups).

The present inventors found a technique capable of appropriately selecting any hydrogen generation rate, any generation gas amount, and any hydrogen generation time using water (e.g., a pH value of 7 or more) using safe silicon, and a composite composition therefor. In addition, as shown below, by elucidating the chemical structure and molecular structure of the silicon fine particle containing a silicon suboxide, and a change in a molecular structure corresponding to the reaction in detail, for the first time, the detailed atomic level situation of the composite composition can be clarified, which provides great technical significance.

First, the silicon suboxide contains many silicon dangling bonds. It is considered that the silicon dangling bonds have an energy level in the band gap of the silicon oxide membrane, and chemical species move in a hopping manner through the energy level. Therefore, the silicon dangling bonds promote the diffusion or migration of chemical species (hydroxide ions ($OH^-$ ions)) which oxidize the silicon fine particle in the silicon oxide membrane. It is considered that the silicon dangling bonds present at the interface between the silicon and the silicon oxide membrane reduce the activation energy of the hydrogen generation reaction.

Here, the present inventors found that the suboxide present in the silicon oxide membrane acts as a chain reaction-mediated active intermediate.

It has been found from the research conducted by the present inventors heretofore that the hydrogen generation due to the reaction between silicon and water can be described by the following chemical reaction formula.

In the chemical reaction formula (1), silicon reacts with hydroxide ions ($OH^-$) to produce $SiO_2$, hydrogen, and electrons (e). This reaction is considered to occur at the interface between the silicon and the silicon oxide membrane. The produced electrons move to the surface of the silicon oxide membrane, and water molecules receive the electrons as shown in the chemical reaction formula (2), whereby hydroxide ions and hydrogen are produced. Therefore, after the whole reaction (chemical reaction formula (1)+chemical reaction formula (2)=chemical reaction formula (3)) occurs, the concentration of the hydroxide ion does not change. Meanwhile, the chemical reaction represented by the chemical reaction formula (1) is a rate-limiting reaction, so that the reaction rate remarkably increases as the concentration of the hydroxide ion increases.

[Chemical Formula 1]

$$Si + 2OH^- \rightarrow SiO_2 + H_2 + 2e \quad (1)$$

$$2H_2O + 2e \rightarrow 2OH^- + H_2 \quad (2)$$

$$Si + 2H_2O \rightarrow 2H_2 + SiO_2 \quad (3)$$

Here, the chemical reaction formula (1) is not a one-step reaction, and is composed of multi-step reactions shown by the following (4) to (7).

[Chemical Formula 2]

$$2Si + OH^- \rightarrow Si_2O + \tfrac{1}{2}H_2 + e \quad (4)$$

$$Si_2O + OH^- \rightarrow 2SiO + \tfrac{1}{2}H_2 + e \quad (5)$$

$$2SiO + OH^- \rightarrow Si_2O_3 + \tfrac{1}{2}H_2 + e \quad (6)$$

$$Si_2O_3 + OH^- \rightarrow 2SiO_2 + \tfrac{1}{2}H_2 + e \quad (7)$$

The amount of the silicon suboxide hardly changed during the hydrogen generation. This is considered to be because the reactions of the chemical reaction formulae (4) to (7) proceed in parallel. The silicon suboxides $Si_2O$, $SiO$, and $Si_2O_3$ are present at the interface between the silicon oxide membrane and the silicon and/or in the silicon oxide membrane. It is considered that, as each reaction proceeds, the silicon suboxide is formed, and the silicon suboxide is further oxidized, which causes an increased amount of silicon dioxide ($SiO_2$). Therefore, it can be said that the above "broadly defined" "silicon oxide" is a mixed composition of the silicon suboxide and silicon dioxide. According to the definition of chemical terms, a substance in which at least the silicon suboxide is present on the surface of the silicon fine particle can be referred to as a "complex". The "composite composition" in the present application is not limited to only the case where it corresponds to the above-described "complex". For example, the "composite composition" of the present application contains the case of "containing a silicon fine particle and a mixed composition of the silicon suboxide and silicon dioxide".

Due to the occurrence of the above-described chemical reaction formulae (5) to (7), hydrogen is generated when the silicon suboxide is oxidized and the silicon dioxide ($SiO_2$) is formed. Since the reactions of the above-described chemical reaction formulae (4) to (7) occur, $OH^-$ ions penetrate into the silicon oxide membrane.

Therefore, by forming the silicon oxide membrane containing many silicon suboxides, and/or the interface between the silicon oxide membrane and a silicon crystal layer, the present inventors obtained the following findings (X) and (Y).

(X) The reaction between the silicon fine particle and moisture (particularly the hydroxide ions ($OH^-$ ions)) is promoted to provide a stronger hydrogen generating capability of the silicon fine particle, that is, lead to the continuous generation or more accurate drawing of a large volume of hydrogen gas for a long time.

(Y) As shown by the above-described reaction formulae (1) to (7), the hydrogen generation rate can be arbitrarily controlled by controlling the pH value utilizing the reaction of the $OH^-$ ions.

As a result, the present inventors realized the silicon fine particle containing many silicon suboxides by manufacturing the silicon fine particle subjected to the above-described devices.

As described above, a suitable state for generating hydrogen was clearly formed, in which the hydrogen generating capability of the silicon fine particle is stronger, that is, a large volume of hydrogen gas is continuously generated for a long time, or is more accurately drawn.

The present inventors realized a silicon fine particle containing many silicon suboxides by subjecting the above-described silicon fine particle to an additional treatment, and also succeeded in changing the silicon fine particle containing a silicon suboxide to hydrophilic silicon fine particle when macroscopically viewed. Specifically, the bonding of many hydroxyl groups (OH groups) on the surface of the silicon oxide membrane was realized by removing the hydrogen atoms bonded to the surface of the silicon oxide membrane having a silicon suboxide contained in the silicon fine particle, and derived from the reaction with silicon atoms. In other words, by realizing many SiOH groups, the silicon fine particle containing the silicon oxide membrane containing a silicon suboxide was hydrophilic when macroscopically viewed. As a result, the silicon fine particle whose the contact or reaction with moisture is promoted can have a stronger hydrogen generating capability, that is, can continuously generate a large volume of hydrogen gas for a long time, or more accurately exhibit the hydrogen generating capability.

As described above, the present inventors found that, by at least partially devising the surface of the silicon fine particle containing a silicon suboxide, the silicon oxide membrane covering the surfaces, and the interface between the surfaces and the silicon oxide membrane, the formation of microscopic physical properties or features leads to a stronger hydrogen generating capability of the silicon fine particle, that is, the continuous generation for a long time or more accurate drawing of a large volume of hydrogen gas. In addition, as a result of further research and development, the present inventors found that a composite composition containing a silicon fine particle at least partially containing a silicon oxide membrane containing such a silicon suboxide is used as a composite composition for oral and external uses. Furthermore, the present inventors found that the hydrogen generation amount required depending on the use, the method for preparing the composite composition, the amount of the composite composition used, the size of the fine particles forming the composite composition, or the pH value, or the like can be arbitrarily adjusted. The present invention was created for the first time by introducing the above-described viewpoints and devices which were different from conventional ones.

One composite composition of the present invention contains: a silicon fine particle; and a silicon suboxide ($SiO_x$, wherein x is ½, 1, or ³⁄₂) and/or a mixed composition of the silicon suboxide and silicon dioxide, at least partially covering a surface of the silicon fine particle.

According to the above-described composite composition, the silicon oxide membrane at least partially covering the surface of the silicon fine particle contains the above-described silicon suboxide, whereby the silicon fine particle can have a stronger hydrogen generating capability, that is, a large volume of hydrogen gas can be continuously generated for a long time, or more accurately drawn.

In the meantime, in the present application, a basic unit of a "diameter" to be measured is expressed as a "crystallite" regardless of the size of the diameter of the crystal (not including the silicon oxide membrane).

The "silicon fine particle" in the present application contains a silicon particle having an average crystallite diameter of a micron level or less, specifically, a crystallite diameter of 1 nm or more and 500 μm or less as a main particle. In a narrower sense, the "silicon fine particle" in the present application contains silicon nanopowder having an average crystallite diameter of a nano level, specifically, a crystallite diameter of 1 nm or more and 50 nm or less (in a broader sense, 1 nm or more and 500 nm or less) as a main particle. In the present application, the "silicon fine particle"

includes not only one in which the silicon fine particles each are dispersed but also one in which a plurality of silicon fine particles aggregate to form aggregates having a size of μm order (generally, 0.1 μm or more and 500 μm or less). The above-described numerical ranges of the "silicon fine particle" are just examples, and the numerical ranges are not limited. The crystallite diameter is appropriately selected depending on the use, use method, and required function and the like of the "silicon fine particle". The "silicon fine particle" may be used in a state of being mixed with other substance as long as the "silicon fine particle" do not provide the hydrogen generating capability. The "silicon oxide" in the present application is a mixed composition of the silicon suboxide and silicon dioxide.

A "water-containing liquid" in the present application is water or an aqueous solution, and contains, for example, a digestive tract fluid of an animal (including human). The "digestive tract fluid" refers to a small intestinal fluid and a large intestinal fluid. Needless to say, the example of the "water-containing liquid" is not limited to the above-described examples. The "pH adjusting agent" in the present application is not particularly limited as long as it is an agent (hereinafter, an "alkali agent") which can adjust the pH value to an alkaline region of more than 7 (typically, more than 7.4). The use of the pH adjusting agent on the skin of an animal (including human) is also included. When the composite composition is used as an in vivo active oxygen neutralizing drug, an alkali agent recognized as a pharmaceutical product (official drug), a quasi-drug, and a food additive is preferably used. As already described, the composite composition is not limited to the use thereof for an animal (including human). Examples of the alkali agent which may be employed include sodium hydrogen carbonate, sodium carbonate, sodium dihydrogen phosphate, disodium hydrogen phosphate, potassium hydrogen carbonate, potassium carbonate, and a pH adjusting agent for a pharmaceutical product, a quasi-drug, a food, or a cosmetic. Among them, sodium hydrogen carbonate, which is the most general-purpose product, is widely used as a pharmaceutical product, a quasi-drug, or a food additive since it has a plurality of advantages such as an excellent pH value adjusting function, safety, and versatility required by the present invention. Meanwhile, in industrial uses, pH adjusting agents can be widely employed without being limited to the above-described pH adjusting agents. As one suitable aspect, any of the pH adjusting agents is not decomposed by an acid. In particular, it is preferable that, when the composite composition of the present application is orally ingested, the composite composition is not decomposed or hardly decomposed by stomach acid.

Effects of the Invention

In one composite composition of the present invention, the silicon oxide membrane at least partially covering the surface of the silicon fine particle contains the above-described silicon suboxide, whereby the hydrogen generating capability of the silicon fine particle can be more strongly or more accurately drawn.

BRIEF DESCRIPTION OF THE DRAWINGS

FIG. 1 shows an XPS spectrum of an Si2p region when the surface state of silicon fine particle of a first embodiment and the surface state of silicon fine particle of modified example (1) of the first embodiment are measured by using an X-ray photoelectron spectroscopy analyzer (XPS analyzer), and an XPS spectrum of an Si2p region when hydrogen is generated by bringing the silicon fine particle of the modified example (1) of the first embodiment into contact with water of about 37° C., and the state of the surface is measured after the elapse of a predetermined time (reaction time). Dotted lines represent the results of the peak separation of the spectra into $Si^0$, $Si^+$, $Si^{2+}$, $Si^{3+}$, and $Si^{4+}$.

FIG. 2 is a graph showing a change in the membrane thickness of a silicon oxide membrane, a change in the membrane thickness of silicon dioxide ($SiO_2$) contained in the silicon oxide membrane, and a change in the membrane thickness of a silicon suboxide ("suboxide" in the figure), calculated based on the measurement results of FIG. 1 with respect to a predetermined time (reaction time) when hydrogen is generated by bringing the silicon fine particle of the modified example (1) of the first embodiment with water.

FIG. 3 shows an FT-IR spectrum of the silicon fine particle having a silicon suboxide after a pulverizing step of the first embodiment (upper), and an FT-IR spectrum of the silicon fine particle having a silicon suboxide after a reforming step of the first embodiment (lower).

FIG. 4 is a conceptual diagram showing structural models regarding a surface of the silicon fine particle at least partially forming a composite composition of the first embodiment, a silicon oxide membrane containing a silicon suboxide covering the surfaces, and/or the interface between the surfaces and the silicon oxide membrane.

FIG. 5 is a graph showing the relationship between a hydrogen generation amount and a reaction time when an aqueous solution containing the silicon fine particle in one example of the modified example (1) of the first embodiment, and having a pH adjusted to 10 by using sodium hydrogen carbonate and sodium carbonate reacts with water of about 36° C.

FIG. 6 is a graph showing the relationship between a hydrogen generation amount and a reaction time when an aqueous solution containing a reformed silicon particle powder in a third embodiment and having a pH adjusted to 8.2 by using sodium hydrogen carbonate reacts with water of about 36° C.

FIG. 7 is a graph showing the relationship between a hydrogen generation amount and a reaction time when an aqueous solution containing a reformed silicon particle powder in modified example (1) of the third embodiment and having a pH adjusted to 8.2 by using sodium hydrogen carbonate reacts with water of about 36° C.

FIG. 8 is a side view showing a laminated structure of a layer shaped body and a medium before hydrogen is generated in other embodiment (3), and FIG. 8(b) is a side view showing the laminated structure of the layer shaped body and the medium when hydrogen is generated in the other embodiment (3).

FIG. 9 is a side view showing a layered structure in modified example of the other embodiment (3).

DESCRIPTION OF REFERENCE SIGNS

10a: Layer shaped body
20: Base part
70: Film which is impermeable to water
90b: Medium
100: Laminated structure
200: Structure

EMBODIMENTS OF THE INVENTION

Embodiments of the present invention will be described in detail with reference to the accompanying drawings.

[1] Composite Composition and Method for Manufacturing the Same

First Embodiment

A composite composition of the present embodiment contains a silicon fine particle having a hydrogen generating capability. In addition, the composite composition of the present embodiment is a novel composite composition in which silicon dioxide ($SiO_2$) and a silicon suboxide ($SiO_X$, wherein x is, ½, 1, and 3/2) is contained in a silicon oxide membrane at least partially covering the surface of the above-described silicon fine particle.

The membrane thickness of the above-described silicon oxide membrane may be varied by generating hydrogen as described later, and the range of the membrane thickness is 0.5 nm or more and 20 nm or less. In addition, the amount of the above-described silicon suboxide contained in the silicon oxide membrane may also be varied by generating hydrogen, and as one suitable example, the composition ratio of the silicon suboxide (ratio of the number of silicon atoms) in the silicon oxide membrane before a hydrogen generation reaction to be described later is 10% or more. It is not particularly necessary to set the upper limit of the composition ratio, and the upper limit is 80% (that is, 80% or less) if it is daringly mentioned.

Next, a method for manufacturing the composite composition of the present embodiment will be described, and the surface of the silicon fine particle measured or observed by various analyzes in some steps of the process, the silicon oxide membrane covering the surfaces, and/or the state of the interface between the surfaces and the silicon oxide membrane will be described.

In the composite composition of the present embodiment, as silicon particles, for example, silicon microscopic particles are used, which are obtained by refining a commercially available high-purity silicon particle powder (manufactured by Kojundo Chemical Laboratory Co., Ltd., particle size distribution <φ 5 µm (typically, silicon particles having a crystal grain size of more than 1 µm, purity: 99.9% i-type 5658 silicon>) by a pulverizing treatment using a bead mill in a liquid such as ethanol. The silicon fine particle contains, for example, silicon nanopowder and/or an aggregate of silicon nanopowder. The present embodiment is not limited to the size, purity, pulverizing method, or dispersion solvent of the silicon particle powder as the raw material of the above-described composite composition. Example employed in an embodiment or modified example other than the present embodiment is also just exemplary, and is not limited to the aspect of the embodiment or modified example.

As specific example, the following pulverizing step is performed. In the pulverizing step, a bead mill device (manufactured by Imex Co., Ltd., RMH type horizontal continuous ready mill) is used, and 200 g of a high-purity silicon particle powder as silicon particles (manufactured by High-purity Chemical Laboratory Co., Ltd., particle size distribution<φ 5 µm, purity: 99.9% or more) is dispersed in a mixed solution of 4000 ml of alcohols such as ethanol, isopropyl alcohol (IPA), or methanol of 99% or more (in the present embodiment, ethanol) and a small amount of water (e.g., 0.1% by weight or more and 10% by weight or less, more suitably more than 1% by weight and 2% by weight or less). Zirconia beads of φ 0.5 µm (volume: 2900 ml) are added thereto, followed by pulverizing in the air at room temperature for 4 hours at a rotation speed of 2500 rpm for refining. As one suitable aspect, the ethanol (e.g., 99.5% by weight) is employed as the alcohols contained in the mixed solution from the viewpoint of improving the accuracy of the safety of the silicon fine particle to be finally manufactured and the composite composition containing the silicon fine particle (e.g., safety to a human body).

As other example of the above-described pulverizing step, for example, when a pulverizing time by a bead mill device was 1 hour, silicon particles were confirmed to be obtained, which contained silicon nanopowder having an average particle diameter of 100 nm or less, silicon fine particles having a size of 40 nm to 0.5 µm and containing the silicon nanopowder, and/or aggregates of the silicon nanopowder and silicon fine particles containing the silicon nanopowder as main particles.

From further studies by the present inventors, the following finding was obtained. A silicon oxide membrane containing more suboxides is formed during or after the pulverizing treatment using a solvent further containing a small amount of water in addition to the above-described solvent. This fact can largely contribute to further improvement in the hydrogen generating capability provided by the silicon fine particle. The present inventors also found that the pulverizing step of the present embodiment provides a more substantial spherical or disk shape of the silicon fine particle. The pulverizing method is not limited to a bead mill pulverizing method. For example, other pulverizing methods such as a high pressure collision method may also be appropriately employed. In addition, the type of the main solvent is also not limited to the ethanol. For example, as the type of the main solvent, other alcohols such as isopropanol, and/or solvents other than alcohols such as acetone, acetonitrile, THF, and acetic acid ester can be used in place of the above-described ethanol or together with the ethanol.

In addition, as described in detail later, the present inventors obtained an interesting finding when analyzing the silicon fine particle (including silicon nanopowder) by FT-IR analysis. Specifically, in the process of manufacturing the silicon fine particle (the above-described pulverizing step), water contained in alcohol (typically, ethanol) and/or water vapor in the air reacts with the silicon fine particle. As a result, it is considered that a slight hydrogen generation reaction occurs. Water molecules are known to be partially dissociatively adsorbed on H and OH in the initial reaction between silicon and water. As a result of a slight reaction with water during the pulverizing step, hydrogen atoms are bonded to silicon atoms at the interface between the silicon fine particle and the silicon oxide membrane, so that Si—$H_3$, Si—$H_2$, and Si—H are considered to be confirmed in FT-IR analysis. Therefore, H—$SiO_3$, H—$SiO_2$ and H—SiO present on the surface of the silicon oxide membrane cause hydrophobicity, and Si—$H_3$, Si—$H_2$, and Si—H present at the interface between the silicon fine particle and the silicon oxide membrane containing a silicon suboxide does not involve hydrophobicity. As described above, the hydrogen atoms bonded to the silicon atoms are easily removed by a surface treatment using hydrogen peroxide.

Thereafter, the mixed solution containing the silicon fine particle (including silicon nanopowder) and separated from beads in a bead mill pulverizer is heated to 40° C. using a reduced pressure evaporator, to evaporate the mixed solution, which makes it possible to obtain a dried silicon fine particle (including silicon nanopowder). The dried silicon fine particle can be stored in a vacuum container, or a container subjected to nitrogen substitution. The methods for separating and drying the silicon nanopowder obtained by pulverizing are not limited to the methods disclosed in the present embodiment. For example, known separation methods and/or drying methods employed in the production of other particles can also be employed.

One example of the silicon fine particle (including silicon nanopowder) obtained by the above method mainly contains silicon nanopowder having a crystallite diameter of 1 nm or more and 500 nm or less. More specifically, as a result of measuring the silicon nanopowder by an X-ray diffractometer (Smart Lab manufactured by Rigaku Corporation), the following values are obtained as an example. In the volume distribution, the crystallite mode diameter, median diameter, and average crystallite diameter of silicon was respectively 6.6 nm, 14.0 nm, and 20.3 nm. The above-described results are merely the results of the pulverizing step and the like as one example, and therefore the present embodiment is not limited to the above-described numerical values.

When one example of the silicon fine particle was observed using a scanning electron microscope (SEM), some of the silicon fine particles aggregated to have a slightly large and irregular shape of about 0.1 μm or more. When each of the aggregates of the aggregating silicon fine particles was observed using a transmission electron microscope (TEM), many of the crystallites contained in the observation field of view had a crystallite diameter of about 2 nm or more and 40 nm or less. The above-described results are merely the results of the pulverizing step and the like as one example, and therefore the present embodiment is not limited to the above-described numerical values.

In the silicon fine particle manufactured through the above-described pulverizing step, as described later, the silicon oxide membrane at least partially covering the surface of the silicon fine particle is enriched in a silicon suboxide, which makes it possible to more strongly or more accurately draw the hydrogen generating capability of the silicon fine particle. More specifically, by employing the silicon fine particle, for example, a high hydrogen generation rate can be realized over a long time of 20 hours or more from the start of hydrogen generation.

Modified Example of First Embodiment (1)

As one suitable aspect, a reforming step of reforming the surface of the silicon fine particle manufactured in the above-described first embodiment by bringing the surfaces into contact with hydrogen peroxide water is performed. By the reforming step, a silicon fine particle including silicon nanopowder can be changed to hydrophilic silicon fine particle when macroscopically viewed. Means for bringing the surface of the silicon fine particle into contact with the hydrogen peroxide water is not limited. For example, the reforming step can be performed by immersing the silicon fine particle in 3% by weight hydrogen peroxide water (e.g., about 10° C. to about 80° C., and about 20° C. to about 50° C. from the viewpoint of realizing a lower cost) accommodated in a known container. The same reforming can also be realized by immersing the silicon fine particle in ozone water and/or sodium percarbonate in place of the hydrogen peroxide water. Alternatively, the same reforming can also be realized by bringing the silicon fine particle into contact with at least one selected from the group consisting of hydrogen peroxide water, ozone water, and sodium percarbonate.

Specifically, by performing the above-described reforming step, the hydrogen atoms adsorbed on the surface of the silicon oxide membrane containing a silicon suboxide contained in the silicon fine particle can be removed, and many hydroxyl groups (OH groups) (that is, SiOH groups) can be caused to be present on the surface of the silicon oxide membrane. This makes it possible to make the silicon fine particle having a silicon suboxide hydrophilic when macroscopically viewed, whereby the silicon fine particle having a silicon suboxide in which the contact or reaction with moisture is more accurately promoted can more strongly or more accurately exhibit a hydrogen generating capability. Therefore, the silicon fine particle having a silicon suboxide (that is, an example of the composite composition) can function as a hydrogen supply material. As described above, it is also suitable that the reforming step is performed using the hydrogen peroxide water having about room temperature from the viewpoint of realizing a low cost and a safe treatment. In addition, as one suitable aspect, the hydrogen peroxide water is employed in the reforming step of the present embodiment from the viewpoint that hydrogen can be generated by using a safer and more reliable material (e.g., having less influence on the human body) like ethanol.

When one example of the silicon fine particle having a silicon suboxide of the present modified example was observed using a scanning electron microscope (SEM), the silicon fine particle partially aggregated to have a slightly large and indefinite shape of about 0.1 μm or more. When each of the aggregates of the aggregating silicon fine particles was observed using a transmission electron microscope (TEM), many of the crystallites contained in the observation field of view had a crystallite diameter of about 2 nm or more and 40 nm or less.

As a result of detailed examination of the generation rate of hydrogen when the silicon fine particle having a silicon suboxide of the present modified example was brought into contact with water, as described later, the generation rate of hydrogen was confirmed to be about 10 times or more faster than the hydrogen generation rate when the silicon fine particle having a silicon suboxide of the first embodiment is brought into contact with water.

In the meantime, in the reforming step of the present embodiment, the hydrogen peroxide water is utilized to reform the surface of the silicon fine particle, but as described above, the material which realizes the reforming step in the modified example (1) of the first embodiment is not limited to the hydrogen peroxide water. As examples other than the above, other aspect which can be employed is also using sodium percarbonate in place of the hydrogen peroxide water. Since sodium percarbonate reacts with water to produce hydrogen peroxide water, the same effects as those of the modified example (1) of the first embodiment can be exhibited.

<Comparative Analysis of First Embodiment with Modified Example (1) of First Embodiment>

Hereinafter, shown are the results of the measurement and consideration of the state of the surface of the silicon fine particle having a silicon suboxide of the first embodiment (including silicon oxide on the surfaces, same as below) and the state of the surface of the silicon fine particle having a silicon suboxide in the modified example (1) of the first embodiment (including silicon oxide on the surfaces, same as below) using various analytical methods.

[XPS Analysis Results]

The present inventors analyzed the surface of the silicon fine particle of the above-described two embodiments (one example of the composite composition) using an X-ray photoelectron spectroscopy analyzer (XPS analyzer) (manufactured by Shimadzu Corporation, model: KRATOS AXIS 165).

FIG. 1 shows an XPS spectrum of an Si2p region when the surface states of the silicon fine particles having a silicon suboxide of the above-described first embodiment and the silicon fine particles having a silicon suboxide of the modified example (1) of the first embodiment are measured in the course of a continuous reaction between the silicon fine particles and water having a pH of 7 and a temperature of 36° C. using an XPS analyzer having a Mg Kα radiation source, and an XPS spectrum of an Si2p region when the surface state of the silicon fine particles of the modified example (1) of the first embodiment is measured after the elapse of a predetermined time (reaction time) when hydrogen is generated by bringing the silicon fine particles into contact with water.

Dotted lines in FIG. 1 represent the results of the peak separation of the spectra into $Si^0$, $Si^+$, $Si^{2+}$, $Si^{3+}$, and $Si^{4+}$. All Si2p peaks include $Si2p_{3/2}$ and $Si2p_{1/2}$ peaks which are separated by 0.61 eV from each other with an intensity ratio of 2:1. In FIG. 1, among the above-described two types of peaks, only the $Si^2p_{3/2}$ peak is shown by a dotted line.

In the analysis, the measurement is performed immediately after the pulverizing treatment (after the pulverizing step in the figure), immediately after the reforming step with hydrogen peroxide water (after the reforming step in the figure), after the elapse of the reaction for 1 hour from the contact of the silicon fine particles subjected to the reforming step with ultrapure water, after the elapse of the reaction for 2 hours from the contact of the silicon fine particles subjected to the reforming step with ultrapure water, after the elapse of the reaction for 4 hours from the contact of the silicon fine particles subjected to the reforming step with ultrapure water, after the elapse of the reaction for 6 hours from the contact of the silicon fine particles subjected to the reforming step with ultrapure water, and after the elapse of the reaction for 24 hours from the contact of the silicon fine particles subjected to the reforming step with ultrapure water. The data immediately after the pulverizing treatment (after the pulverizing step in the figure) in FIG. 1 is also employed as the results for the silicon fine particles having a silicon suboxide of the above-described first embodiment.

FIG. 2 is a graph showing a change in the membrane thickness of silicon dioxide ($SiO_2$) (white circle marks in FIG. 2) calculated based on the measurement results in FIG. 1 with respect to a predetermined time (reaction time) when hydrogen is generated by continuously bringing silicon fine particles having a silicon suboxide of the modified example (1) of the first embodiment into contact with water having a pH of 7 and a temperature of 36° C., a change in the membrane thickness of the silicon suboxide ($SiO_x$, wherein x is ½, 1, and 3/2) (triangle marks in FIG. 2), and a change in the membrane thickness (black circle marks in FIG. 2) of a mixed composition of the silicon suboxide and the silicon dioxide (that is, silicon oxide). The reaction time in these analyzes means a contact time when the silicon fine particles are continuously brought into contact with pure water having a pH of 7. Each of the above-described membrane thicknesses can be calculated based on the integrated intensity ratio of the peak of the Si2p region. The membrane thickness of the above-described silicon oxide membrane is a membrane thickness when the membrane thicknesses of the components of the silicon dioxide and the silicon suboxide are summed.

Here, each of the above-described membrane thicknesses is calculated using a method described below based on the integrated intensity ratio of the peaks in the Si2p region as described below.

<Calculation Method of Membrane Thickness>

The XPS spectrum of the Si2p region is separated into peaks of $Si^+$, $Si^{2+}$, $Si^{3+}$, and $Si^{4+}$. Here, $Si^0$, $Si^+$, $Si^{2+}$, $Si^{3+}$, and $Si^{4+}$ mean that the number of oxygen atoms bonded to one silicon atom is 0, 1, 2, 3, and 4. All Si2p peaks include $Si2p_{3/2}$ (high energy side) and $Si2p_{1/2}$ (low energy side) which are separated by 0.61 eV from each other with intensity of 2:1. When the area intensity of the peak due to the silicon oxide membrane is taken as I(oxide), the following formula is given.

[Expression 1]

$$I(\text{oxide}) = I(Si^{4+}) + I(Si^{3+}) + I(Si^{2+}) + I(Si^+) \quad (1)$$

Here, $I(Si^{4+})$, $I(Si^{3+})$, $I(Si^{2+})$, and $I(Si^+)$ are the area intensities of the peaks of $SiO_2$, $Si_2O_3$, $SiO$, and $Si_2O$. The thickness ($t_{oxide}$) of the silicon oxide membrane is given by the following formula using I(oxide) and the area intensity of the Si2p peak of the silicon fine particles, $I(Si^0)$. In the formula, the silicon fine particles are assumed to have a cylindrical shape having a radius R and a height equal to the radius R. (O. Renault, R. Marlier, N. T. Barrett, E. Martinez, T. Baron, M. Gely, and B. De Salvo, Modeling the XPS Si 2p core-level intensities of silicon nanocrystals for determination of oxide shell thickness, Surf. Interface Anal. 38, 486-488 (2006))

[Expression 2]

$$\frac{I(\text{oxide})}{I(Si^0)} = \frac{N_{oxide}\sigma_{oxide}\lambda_{oxide}}{N_{Si}\sigma_{Si}\lambda_{Si}} \cdot \frac{(R-t_{oxide})^2\left[1-\exp\left(\frac{t_{oxide}}{\lambda_{oxide}}\right)\right]+ t_{oxide}(2R-t_{oxide})\left[1-\exp\left(-\frac{H}{\lambda_{oxide}}\right)\right]}{(R-t_{oxide})^2\exp\left(-\frac{t_{oxide}}{\lambda_{oxide}}\right)} \cdot \left[1-\exp\left(-\frac{H-t_{oxide}}{\lambda_{Si}}\right)\right] \quad (2)$$

Here, N is a number density of silicon atoms; σ is a photoionization cross section; λ is an average free path of photoelectrons; and subscript oxide and Si are values of the silicon oxide membrane and silicon fine particles. As ($\sigma_{oxide}/\sigma_{Si}$), $\lambda_{oxide}$, and $\lambda_{Si}$, values of 1.1, 2.9 nm, and 2.5 nm were respectively used, which were described in the literatures (M. F. Hochelia, Jr. and A. H. Carim, Surf Sci. Lett. 197, L260 (1988); and H. Kobayashi, Asuha, O. Maida, M. Takahashi, and H. Iwasa, Nitiric acid oxidation of Si to form ultrathin of Si to form ultrathin silicon dioxide layers with a low leakage current density, J. Appl. Phys. 94 (11) 7328-7335 (2003)).

The number density of the silicon atoms in the silicon oxide membrane, $N_{oxide}$, is given by the following formula.

[Expression 3]

$$N_{oxide} = \frac{N(SiO_2)I(Si^{4+}) + N(Si_2O_3)I(Si^{3+}) + N(SiO)I(Si^{2+}) + N(Si_2O)I(Si^+)}{I(\text{oxide})} \quad (3)$$

Here, $N(SiO_2)$, $N(Si_2O_3)$, $N(SiO)$, and $N(Si_2O)$ respectively represent the atomic densities of the silicon atoms in $SiO_2$, $Si_2O_3$, $SiO$, and $Si_2O$.

The membrane thickness ($t_{SiO2}$) of the silicon dioxide membrane and the membrane thickness ($t_{suboxide}$) of the suboxide are obtained from the following formula using the membrane thickness ($t_{oxide}$) of the silicon oxide membrane.

[Expression 4]

$$t_{SiO2} : t_{suboxide} = \frac{I(SiO_2)}{N(SiO_2)} : \frac{I(suboxide)}{N(suboxide)} \quad (4)$$

$$t_{SiO2} + t_{suboxide} = t_{oxide} \quad (5)$$

Here, $N_{suboxide}$ is given by the following formula (6).

[Expression 5]

$$N_{suboxide} = \frac{N(Si_2O_3)I(Si^{3+}) + N(SiO)I(Si^{2+})}{I(Si^{3+}) + I(Si^{2+}) + I(Si^{+})} \quad (6)$$

<Analysis of Each of Analysis Results>

As shown in FIG. 1, an $Si^0$ peak of the silicon fine particles, a wide $Si^{4+}$ peak of the silicon dioxide ($SiO_2$) membrane, and peaks of $Si^+$, $Si^{2+}$, and $Si^{3+}$ as suboxides, as shown in the area surrounded by the broken line in the figure were observed.

In FIG. 1, when the results immediately after the pulverizing treatment (corresponding to the silicon fine particles having a silicon suboxide of the first embodiment) were compared with the results immediately after the reforming step with hydrogen peroxide water of the modified example (1) of the first embodiment (after the reforming step in FIG. 1), almost no change in $Si^{4+}$ peak intensity of the silicon dioxide ($SiO_2$) membrane was observed. As shown in FIG. 2, in the results immediately after the pulverizing treatment (after the pulverizing step in FIG. 2, corresponding to the silicon fine particles having a silicon suboxide of the first embodiment), and the results immediately after the reforming step with hydrogen peroxide water of the modified example (1) of the first embodiment (after the reforming step in FIG. 1), the membrane thickness of the silicon dioxide ($SiO_2$) was confirmed to hardly change. In addition, the membrane thickness of the silicon oxide shown in FIG. 2 agreed well with an oxide membrane thickness obtained from the observation of a cross-sectional electron micrograph.

As shown in FIG. 1, as the reaction time for generating hydrogen increased, the intensity of the peak based on the silicon dioxide increased, so that the membrane thickness of the silicon dioxide membrane was confirmed to increase with the elapse of the reaction time. In this analysis, the membrane thickness of the silicon dioxide membrane measured after the completion of the hydrogen generation reaction was 10.5 nm. It is particularly worth mentioning that the thick silicon oxide membrane of 10.5 nm is formed under the condition of a very low temperature of 36° C. As described above, in particular, the realization of the thick silicon oxide membrane can be said to be one of typical effects due to the following: the silicon fine particles of the modified example (1) of the first embodiment is enriched in a silicon suboxide; abundant OH groups (that is, SiOH groups) are present on the silicon oxide membrane; and/or the surface has hydrophilicity since almost no hydrogen atoms are present on the surface.

The present inventors obtained the membrane thickness of the silicon dioxide membrane and the membrane thickness of the silicon suboxide in the silicon oxide membrane immediately after the reforming step with hydrogen peroxide water of the modified example (1) of the first embodiment (after the reforming step in FIG. 1) from the XPS spectrum of FIG. 1. As a result, the membrane thickness of the silicon dioxide membrane formed on the surface of the silicon fine particle was 1.7 nm, and the membrane thickness of the silicon suboxide was 1.0 nm.

Therefore, the above-described calculation results prove that the silicon oxide membrane of about 2.7 nm formed on the surface of the silicon fine particle contains many suboxides. The silicon suboxide contains many silicon dangling bonds. It is considered that the silicon dangling bonds have an energy level in the band gap, and chemical species (such as hydroxide ions (OH ions) and the like) which oxidize the silicon fine particles are conducted in a hopping manner through the energy level, which promotes the diffusion (or migration) of the chemical species. Therefore, as it were, the silicon suboxide can be said to act as an active intermediate, as described above.

According to the research and analysis by the present inventors, the present inventors found that, when the relationship between the number of first silicon atoms ($A_1$) of the silicon dioxide and the number of second silicon atoms ($A_2$) of the silicon suboxide in the silicon oxide membrane satisfies the following formula (7), particularly, the hydrogen generating capability of the silicon fine particles can be more strongly or more accurately drawn. Therefore, the composition ratio of the silicon suboxide (ratio of the number of silicon atoms) in the silicon oxide membrane is 10% or more, whereby the hydrogen generating capability which is continuous for a longer time can be more strongly or more accurately drawn. In FIG. 1, the composition ratio of the silicon suboxide (ratio of the number of silicon atoms) in the silicon oxide membrane immediately after the pulverizing treatment (corresponding to the silicon fine particles of the first embodiment) was about 38% according to one experimental result depending on the sample. The composition ratio of the silicon suboxide (ratio of the number of silicon atoms) in the silicon oxide membrane immediately after the reforming step with the hydrogen peroxide water of the modified example (1) of the first embodiment was about 28% according to one experimental result depending on the sample. The hydrogen generation amount by the composite composition in the above-described embodiment or modified example can be arbitrarily adjusted to a required amount by the method for preparing the composite composition, the amount of the composite composition used, the size of the fine particles forming the composite composition, or the pH value or the like, depending on the use.

[Expression 6]

$$\frac{A_2}{A_1 + A_2} \times 100 \geq 10 \quad (7)$$

In addition, in particular, from the viewpoint of more strongly or more accurately drawing the hydrogen generating capability, the composition ratio of the silicon suboxide (ratio of the number of silicon atoms) in the silicon oxide membrane is 10% or more regardless of a pulverized product or a product obtained by surface-treating the pulverized product with hydrogen peroxide or the like. The upper limit of the composition ratio is not particularly limited, and the upper limit is 80% (that is, 80% or less) if it is daringly mentioned. As one more suitable aspect, the above-described numerical range is 20% or more and 70% or less.

As described above, both the silicon fine particles of the first embodiment and the silicon fine particles of the modified example (1) of the first embodiment form the silicon oxide membrane containing many silicon suboxides, and/or the interface between the silicon oxide membrane containing many silicon suboxides and the silicon crystal layer, to promote the reaction between the silicon fine particles and the hydroxide ions (OH⁻ ions). As a result, by employing the silicon fine particles having a silicon suboxide of the first embodiment and the silicon fine particles having a silicon suboxide of the modified example (1) of the first embodiment, the hydrogen generating capability of the silicon fine particles can be more strongly drawn, that is, a large volume of hydrogen can be generated in the body for a long time, or the hydrogen generating capability can be more accurately drawn.

Meanwhile, as shown in FIG. 2, it was confirmed that, while the membrane thickness of the silicon suboxide observed at the intermediate stage of the hydrogen generation reaction is substantially constant, only the membrane thickness of the silicon dioxide increases. This proves that the chemical reactions represented by the chemical reaction formulae (4) to (7) already described proceed at substantially the same time. This result also indicates that the silicon suboxide acts as a chain reaction-mediated active intermediate.

[FT-IR Analysis Results]

The present inventors further analyzed the surface of the silicon fine particle having a silicon suboxide immediately after the pulverizing treatment in the first embodiment, and the surface of the silicon fine particle having a silicon suboxide immediately after the reforming step with hydrogen peroxide water of the modified example (1) of the first embodiment using a Fourier transform infrared spectroscope (FT-IR apparatus) (model: FTIR-6200, manufactured by JASCO Corporation). FIG. 3 shows an FT-IR spectrum of the silicon fine particles having a silicon suboxide after the pulverizing step, and an FT-IR spectrum of the silicon fine particles having a silicon suboxide after the reforming step. For the simplicity of the figure, the lower spectrum is shown with the intensity being quadruple of that of the upper spectrum.

By this FT-JR analysis, the surface concentration of the OH groups (that is, SiOH groups) on the surface of the silicon fine particle having a silicon suboxide immediately after the pulverizing treatment in the first embodiment is calculated to be $1.5 \times 10^{14}/cm^2$ using the following method.

First, the membrane thickness of the silicon oxide membrane is obtained from the XPS spectrum of the Si2p region. The same cylindrical structural model as that used when the membrane thickness of the silicon oxide membrane is obtained from the XPS spectrum in the Si2p region is assumed.

In this model, the volume V of silicon oxide is given by the following formula (8).

[Expression 7]

$$V = \pi(R+t)^3 - \pi R^3 = \pi t(3R^2 + 3Rt + t^2) \quad (8)$$

Meanwhile, the surface area S of the silicon oxide membrane is given by the following formula (9).

[Expression 8]

$$S = \pi(R+t)^2 + 2\pi(R+t)^2 = 3\pi(R+t)^2 \quad (9)$$

The area intensity I(LO) of the LO peak of the silicon oxide membrane is proportional to the volume of the silicon oxide membrane, the atomic density N(oxide) of silicon atoms in the silicon oxide membrane, and the oscillator strength σ(LO) of O—Si—O antisymmetric stretching vibration (LO phonon). Meanwhile, the area intensity I(OH) of the O—H stretching vibration peak of the OH groups present on the surface is proportional to the surface area of the silicon oxide membrane, the surface concentration c(OH) of the OH groups, and the oscillator strength σ(OH) of O—H stretching vibration. Therefore, the ratio (I(OF)/I(LO)) of the peak intensity of the O—H stretching vibration to the peak intensity of the LO phonon is obtained by the following formula (10).

[Expression 9]

$$\frac{I(OH)}{I(LO)} = \frac{3(R+t)^2 c(OH)\sigma(OH)}{t(3R^2 + 3Rt + t^2)N(\text{oxide})\sigma(LO)} \quad (10)$$

The surface concentration of the OH groups on the surface of the silicon fine particle having a silicon suboxide immediately after the pulverizing treatment in the first embodiment before a hydrogen peroxide treatment was $2 \times 10^{14}/cm^3$. The surface concentration was calculated using the formula (9). Meanwhile, the surface concentration of the OH groups on the surface of the silicon fine particle having a silicon suboxide immediately after the reforming step with hydrogen peroxide water was $4.5 \times 10^{14}/cm^3$. The surface concentration of the OH groups estimated using the above method agreed well with a value calculated using the area intensity of a vibration peak based on calcium carbonate and its oscillator strength when a standard sample obtained by mixing 10% by weight calcium carbonate into silicon fine particles was used. It is particularly worth mentioning that the numerical value immediately after the reforming step is twice or more of the surface concentration of the OH groups on the surface of the silicon fine particle having a silicon suboxide immediately after the pulverizing treatment in the first embodiment.

As shown in FIG. 3, the FT-IR spectrum in the Si—H stretching vibration region is separated into six peaks, i.e., a peak due to H—SiO₃ at 2240 cm⁻¹, a peak due to H—SiO₂ at 2192 cm⁻¹, a peak due to H—SiO at 2155 cm⁻¹, a peak due to Si—H₃ at 2135 cm⁻¹, a peak due to Si—H₂ at 2110 cm⁻¹, and a peak due to Si—H at 2077 cm⁻¹. H—SiO₃, H—SiO₂, and H—SiO are due to hydrogen atoms bonded to the surface of the silicon oxide membrane. Meanwhile, as already described, Si—H₃, Si—H₂, and Si—H are manufactured as follows. Water contained in ethanol and/or water vapor in the air, and silicon fine particles react with each other in the process of manufacturing the silicon fine particles (the above-described pulverizing step), to provide a slight hydrogen generation reaction, as a result of which the hydrogen atoms are bonded to silicon atoms at the interface between the silicon fine particles and the silicon oxide membrane.

In the silicon fine particles having a silicon suboxide after the pulverizing step, as shown in FIG. 3, it is found that the surface of the silicon fine particle are at least partially covered with the thin silicon oxide membrane, and the hydrogen atoms are bonded to the surface of the silicon oxide membrane. As a result, as it were, the surface of the silicon oxide membrane macroscopically exhibit hydrophobicity. Therefore, H—SiO₃, H—SiO₂, and H—SiO present on the surface of the silicon oxide membrane cause the hydrophobicity. However, it is considered that Si—H$_3$, Si—H$_2$, and Si—H present at the interface do not participate in the hydrophobicity.

The peak intensities of stretching vibrations due to H—SiO$_3$, H—SiO$_2$, and H—SiO in the silicon fine particles having a silicon suboxide immediately after the reforming step with the hydrogen peroxide water of the modified example (1) of the first embodiment are significantly reduced, so that the hydrogen atoms bonded to the surface of the silicon oxide membrane are removed. It was revealed that the total concentration of H—SiO$_3$, H—SiO$_2$, and H—SiO on the surface of the silicon fine particle before the reforming step is $1.8\times10^{14}/cm^2$, but the concentration after the reforming step is $4\times10^{13}/cm^2$. As a result, it was found that the hydrogen atoms on the silicon oxide membrane are removed by the reforming step using hydrogen peroxide water.

It is found that the peak intensity of the Si—H stretching vibration due to H—SiO$_3$ at 2252 cm$^{-1}$ and the peak intensity of the Si—H stretching vibration due to H—SiO$_2$ at 2192 cm$^{-1}$ observed in the silicon fine particles having a silicon suboxide after the pulverizing step, and the peak intensity of the Si—H stretching vibration due to H—SiO at 2155 cm$^{-1}$ is significantly reduced by performing the reforming step. It is particularly worth mentioning that the above-described H—SiO$_2$ and H—SiO are produced by bonding the hydrogen atoms to the suboxide.

As described above, it is found that the concentration of the hydroxyl groups (OH groups) present on the surface of the silicon oxide membrane containing a silicon suboxide is $5\times10^{13}/cm^2$ or more. Meanwhile, in the silicon fine particles having a silicon suboxide after the reforming step, the hydrogen atoms bonded to the surface of the silicon oxide membrane are removed as described above. Therefore, it can be said that the hydrogen atoms are removed until the concentration of the SiH groups on the surface of the silicon fine particle is $2\times10^{14}/cm^2$ or less. Many hydroxyl groups (OH groups) were also confirmed to be present on the surface of the silicon oxide membrane having a silicon suboxide. As a result of combination of the above-described factors, as it were, the surface of the silicon fine particle having a silicon suboxide can be said to change to hydrophilic surfaces.

Based on the above-described analysis results, the present inventors considered that each of the states of the surfaces of the silicon fine particles, the silicon oxide membrane covering the surfaces, and/or the interface between the surfaces and the silicon oxide membrane changes according to the following structural model in each of the already described chemical reactions.

FIG. 4 is a conceptual diagram showing structural models regarding the surface of the silicon fine particle having a silicon suboxide at least partially forming the composite composition of the present embodiment, the silicon oxide membrane containing a silicon suboxide covering the surfaces, and/or the interface between the surfaces and the silicon oxide membrane. (a) to (d) show the following states:

(a) after the pulverization step
(b) after the reforming step;
(c) when the hydrogen generation reaction proceeds by contacting with water having a pH of 7 (the reaction time is about 6 hours or more); and
(d) when the hydrogen generation reaction is completed.

As shown in FIG. 4, first, after the pulverizing step, the silicon fine particles are covered with the silicon oxide membrane having a thickness of about 2.5 nm. H—SiO$_3$, H—SiO$_2$, and H—SiO are present on the surface of the silicon oxide membrane (FIG. 4(a)). As described above, since H—SiO$_3$, H—SiO$_2$, and H—SiO are present, as it were, the surface of the silicon oxide membrane macroscopically exhibit hydrophobicity, so that the reactivity with water is not so great. Many suboxides are contained in the silicon oxide membrane and/or at the interface between the silicon fine particles and the silicon oxide membrane, as shown in FIG. 4(a).

Then, the surface of the silicon oxide membrane is dramatically changed by performing a reforming step. Since many H—SiO$_3$, H—SiO$_2$, and H—SiO are removed by the reforming step, as it were, the surface of the silicon oxide membrane is hydrophilic, which provides significantly improved reactivity with water (FIG. 4(b)). As shown in FIG. 4(b), many hydroxyl groups (OH groups) are present on the surface of the silicon oxide membrane. Also at this stage, many suboxides are contained in the silicon oxide and/or at the interface between the silicon fine particles and the silicon oxide.

Furthermore, when the contact with water causes the hydrogen generation reaction to proceed (FIG. 4(c)), the reaction rate of the silicon suboxide produced from the silicon fine particles and the reaction rate of the silicon dioxide produced from the silicon suboxide are substantially equal to each other. As a result, the amount of the silicon dioxide (membrane thickness) increases while the silicon suboxide is substantially constant. For example, when the membrane thickness of the silicon dioxide membrane is about 15 nm, the hydrogen generation reaction stops (FIG. 4(d)). The thickness of 15 nm described in FIG. 4 is merely an example, and the present embodiment is not limited to the numerical value. According to the analysis by the present inventors, it is found that the membrane thickness of the silicon oxide membrane (including the silicon dioxide and the silicon suboxide) is 3 nm or more and 20 nm or less (typically 15 nm or less) after the elapse of 168 hours (7 days) from the time of hydrogen generation when the silicon fine particles having a silicon suboxide subjected to the pulverizing step and the reforming step of the present embodiment are brought into contact with water. Therefore, if the membrane thickness of the silicon oxide membrane after the elapse of 168 hours (7 days) from the time of hydrogen generation is within the above-described numerical range, the silicon fine particles of the present embodiment can be accurately recognized. The reaction between the silicon fine particles and water is not limited to this condition. Examples of other conditions include reaction conditions of a pH of 10 and a temperature of 36° C. shown in FIG. 5.

As described above, by performing the pulverizing step and reforming step of the present embodiment, the hydrogen atoms adsorbed on the surface of the silicon oxide membrane included in the silicon fine particles having a silicon suboxide can be removed, and many hydroxyl groups (OH groups) can be caused to be present on the surface of the silicon oxide membrane containing a silicon suboxide. This makes it possible to make the silicon fine particles hydrophilic when macroscopically viewed, whereby the hydrogen generating capability of the silicon fine particles in which the contact or reaction with moisture is more accurately promoted can be more strongly exhibited, that is, a large volume of hydrogen can be generated in the body for a long time, or the hydrogen generating capability can be more accurately exhibited. As described above, it is also suitable that the reforming step is performed using the hydrogen peroxide water having about room temperature from the viewpoint of realizing a low cost and a safe treatment.

Modified Example (2) of First Embodiment

In the meantime, in the first embodiment and the modified example (1) of the first embodiment, the reforming step is performed by immersing the silicon fine particles in the hydrogen peroxide water having about room temperature. Means of the reforming step is not limited to the means disclosed in the modified example (1) of the first embodiment. For example, other aspect which can be employed is also bringing the hydrogen peroxide water into contact with the silicon fine particles using a known ball mill machine in place of immersing the silicon fine particles in the hydrogen peroxide water.

In the present modified example (2), for example, a commercially available high-purity silicon particle powder (particle size distribution<φ 1 mm (typically, silicon particles having a crystal grain size of more than 100 μm), purity. 99.9%) as silicon particles is subjected to a pulverizing treatment according to a ball mill method using stainless balls each having a diameter of 5 mm in a mixed solution of ethanol and water in the same manner as in the first embodiment in the air using a ball mil machine. As a result, by separating the balls and the primary silicon particles from each other in the air, silicon particles having an average particle diameter of 3 μm can be obtained.

Other aspect which can be employed is also further subjecting the silicon particles obtained by the present modified example (2) to a pulverizing step using the bead mill device in the first embodiment to obtain the same silicon fine particles having a silicon suboxide as that in the first embodiment.

In the above-described "other aspect", silicon fine particles mainly having a silicon suboxide having a crystallite diameter of 5 nm or more and 500 nm or less in a volume distribution are contained as a main component. More specifically, the following values were obtained as a result of measuring the silicon fine particles having a silicon suboxide with an X-ray diffractometer. In the volume distribution, the crystallite mode diameter, median diameter, and average crystallite diameter of silicon was respectively 9.3 nm, 26.1 nm, and 41.5 nm. When the silicon fine particles were observed using a SEM, the silicon fine particles having a silicon suboxide partially aggregated to form slightly greater aggregates of 0.5 to 5 μm having an indefinite shape. When the individual silicon fine particles were observed using a TEM, many of them had a crystallite diameter of about 5 nm or more and 50 nm or less.

Modified Example (3) of First Embodiment 5 mg of the silicon fine particles of the first embodiment, the modified example of the first embodiment (1), or the modified example of the first embodiment (2) are mixed with about 500 mg of a sodium hydrogen carbonate powder (manufactured by Wako Pure Chemical Industries, Ltd., purity: 99.5%). This mixture is kneaded, and a tableting method is used, whereby a tablet can be obtained as a cylindrical mass having a diameter of about 8 mm and a height of about 4 mm. The tablet is an example of a lump preparation. One suitable aspect is a nanocapsule, a microcapsule, an ordinary capsule, or coating in which silicon fine particles having a stable silicon suboxide and a pH adjusting agent such as sodium hydrogen carbonate are separately stable under an acidic condition and dissolved under a basic condition. By employing the above-described aspect, it is possible to avoid the reaction in the presence of moisture under an acidic condition and promote the reaction of the silicon fine particles with water by being dissolved in the presence of moisture in a basic condition.

Modified Example (4) of First Embodiment

In the first embodiment and the modified example (1) of the first embodiment, a mixed solution of ethanol and a small amount of water (0.1% by weight to 2% by weight) is employed in a pulverizing step using a bead mill, but the first embodiment is not limited to the mixed solution. For example, even when 2-propanol is employed, or the various solvents already described are employed, in place of ethanol, the same effects as those of the first embodiment or the modified example (1) of the first embodiment can be exhibited.

Second Embodiment

As one of characteristics of the composite composition of the present embodiment, the composite composition is manufactured by performing a pulverizing step using an acidic solution (typically, a pH value of 3 to 6) in place of ethanol and a small amount of water employed in the pulverizing step in the first embodiment. The description overlapping with that of the first embodiment may be omitted.

The raw material of the composite composition in the present embodiment is, for example, a high-purity silicon particle powder (particle diameter: 300 μm or less) obtained by pulverizing commercially available i-type polycrystalline silicon having a purity of 99.99% or more using a jet mill method, and sieving the pulverized product with a 300-μm sieve. The present embodiment is not limited to the size, purity, pulverizing method, or dispersion solvent of the silicon particle powder as the raw material of the above-described composite composition.

As a specific example, a bead mill device (manufactured by Imex Co., Ltd., RMH type horizontal continuous ready mill) is used. In the bead mill device, a pulverizing step is performed. In the pulverizing step, 2.1 g of the above-described high-purity silicon particle powder as silicon particles is dispersed in 78 mL of an acidic solution adjusted to a pH value of 3 to 5 (in the present embodiment, hydrochloric acid (HCl aqueous solution)), and zirconia beads of φ 0.5 μm (volume: 2900 ml) are then added thereto. The mixture is pulverized for finely dividing at a rotation speed of 2500 rpm in the air for 75 minutes in a state where the temperature of cooling water of the bead mill device is set at about 6° C. The pH adjusting solution for forming the acidic solution is not limited to hydrochloric acid. For example, as one suitable aspect, the pH value is 5 or 6 from the viewpoint of improving the accuracy of the safety (e.g., safety for the human body) of the finally manufactured silicon fine particle (including silicon nanopowder and/or an aggregate of the silicon nanopowder) and the composite composition containing the silicon fine particles.

It was confirmed that, even when the manufacturing method of the composite composition of the present embodiment is employed, the effects exhibited by the composite composition of the first embodiment and the manufacturing method thereof can be at least partially obtained.

[XPS Analysis Results]

The present inventors analyzed the surface of the silicon fine particle (composite composition) of the present embodiment as one example using an X-ray photoelectron spectroscopy analyzer (XPS analyzer) (manufactured by Shimadzu Corporation, model: KRATOS AXIS 165).

Regarding the silicon fine particles to be analyzed, the pH value of the acidic solution used in the above-described pulverizing step is 5.0. As a result of analysis of the observed XPS spectrum, the silicon fine particles formed by pulverizing with a bead mill method using hydrochloric acid (HCl aqueous solution) having a pH of 5.0 were found to have a 1.6-nm silicon dioxide membrane, a 1.0-nm silicon suboxide, and a 2.6-nm silicon oxide membrane.

Third Embodiment

A composite composition of the present embodiment is characterized in that it is formed without performing the pulverizing step in each of the first and second embodiments. The description which overlaps with that of the first or second embodiment, or each of modified examples thereof may be omitted.

The raw material of the composite composition in the present embodiment is the high-purity silicon particle powder (particle diameter: 300 μm or less) of the second embodiment. The present embodiment is not limited to the size, purity, pulverizing method, or dispersion solvent of the silicon particle powder as the raw material of the above-described composite composition.

In the present embodiment, the pulverizing step is not performed, but as with the modified example (1) of the first embodiment, a reforming step for reforming the surface of the silicon particle powder by bringing the surface into contact with hydrogen peroxide water is performed. Specifically, the reformed silicon particle powder of the present embodiment (one example of the composite composition) is formed by bringing hydrogen peroxide water having a concentration of, for example, 3% by weight into contact with the silicon particle powder for 30 minutes.

Then, 78 ml of water (aqueous solution) having a pH adjusted to 8.2 and a temperature of 36° C. using sodium hydrogen carbonate was added to prepare an aqueous solution, and the reformed silicon particle powder was dispersed in the aqueous solution. In the present embodiment, the amount of hydrogen gas generated by immersing the reformed silicon particle powder in the aqueous solution was measured using a hydrogen concentration meter. FIG. 6 is a graph showing the relationship between an amount of hydrogen gas generated and a reaction time in the present embodiment.

Modified Example (1) of Third Embodiment

As one modified example of the present embodiment, an example (modified example) in which the same treatment as that of the third embodiment is performed will be described except that a 300-μm sieve employed in the process of forming the reformed silicon particle powder in the third embodiment is changed to a 45-μm sieve.

In the present embodiment, a reformed silicon particle powder (one example of a composite composition) having a particle diameter of 45 μm or less is formed. FIG. 7 is a graph showing the relationship between an amount of hydrogen gas generated and a reaction time in the present modified example.

As described above, also in the third embodiment and modified example thereof, the generation of hydrogen which can be said to be a sufficient amount in a relatively short time could be confirmed. Therefore, even when the composite composition is formed without performing the pulverizing step in the first or second embodiment, the effects of the first or second embodiment can be at least partially exhibited.

Other Embodiment (1)

The composite composition of each of the above-described embodiments or modified examples thereof can be utilized as a preparation, for example. In addition, the utilization example thereof is not limited to a tablet. For example, even when a capsule preparation with a powdery composite composition encapsulated in a capsule is employed in place of a tablet, the same effects as the above-described effects can be exhibited. The composite composition can generate much hydrogen when the composite composition is in the powdery form having a large surface area rather than being in a lump form, but the composite composition is orally ingested easily when formed into a tablet or a capsule preparation. When the composite composition is formed into a tablet or a capsule preparation, it maintains a lump form to some extent in the stomach, but is increasingly disintegrated to assume a powdery form after passing through the stomach. Therefore, in the stomach where it is desired to suppress the hydrogen generation reaction, the surface area of the composite composition exposed to gastric fluid and/or gastric contents can be reduced, and in the small intestine and/or large intestine where it is desired to promote the hydrogen generation reaction, the surface area of the composite composition exposed to the water-containing liquid can be increased.

The composite composition may be a granular preparation. The granular preparation assumes a powdery form in an earlier stage after being orally ingested as compared with tablets and capsules. However, since the pH value of gastric fluid is low (about 1.5), the preparation generates little hydrogen even when assuming a powdery form immediately after reaching the stomach, and generates hydrogen in the presence of water after passage through the stomach.

The complex composition may be a powdered preparation. The powdered preparation is easy to handle when the composite composition is used as, for example, a constituent component of a food such as a health food, for example, a food additive. When the composite composition is used as a food additive, silicon particles having a crystallite diameter of 1 nm or more and 10 μm or less or 1 nm or more and 500 nm or less (in a narrower sense, 1 nm or more and 100 nm or less) may be mixed and used as the composite composition. It is preferable that the silicon fine particles are contained in an amount of 1% by mass or more. The upper limit of the content of the silicon fine particles is not specified, but it is preferably 40% by mass or less in consideration of the taste.

An example of a coating layer which can be applied to a tablet is a known enteric material hardly soluble in the stomach, which is a coating agent which covers the outermost layer of the tablet. An example of a coating layer which can be applied to a capsule preparation is a capsule itself which encapsulates the composite composition, and is manufactured from a known enteric material hardly soluble in the stomach.

As described above, an example of a preparation suitable as a utilization example of the complex composition is a tablet which is a lump preparation which is easily orally ingested in a sufficient amount, or a capsule preparation in which the powdery complex composition (may contain those formed into aggregates) are encapsulated in a capsule. When a tablet is employed, a disintegrating agent may be further contained. For the disintegrating agent, a known material can be employed. In addition, a suitable example of a more suitable disintegrating agent is an organic acid, and the most suitable example is citric acid. Here, the organic acid can also function as a binding agent which brings silicon fine particles or silicon nanopowder into a lump form. The composite composition can be utilized as, for example, a granular, flake-like, and/or powdered food topping material (typically, "furikake") for each food material.

Other Embodiment (2)

In the composite composition of each of the above-described embodiments or modified examples thereof, for example, by using a "medium" brought into contact with the composite composition, hydrogen can be dermally or transmucosally taken in the body (including the skin itself or the mucous membrane itself). The medium of the present embodiment does not particularly limit the material or the product. A physiologically acceptable medium can exhibit the effects of the present embodiment. Therefore, one containing the composite composition and the medium brought into contact with the composite composition can exhibit a function as a hydrogen supply material.

One specific suitable example of the medium is at least one selected from the group consisting of a liquid form, a gel form, a cream form, a paste form, an emulsion form, and a mousse form, from the viewpoint of increasing the opportunity of the human body site brought into contact with water (or a water-containing liquid) or a medium containing the water (or the water-containing liquid) (hereinafter, also referred to collectively as a "medium") in life scenes. Another suitable example of the medium is bathwater (suitably alkaline bathwater). Therefore, in one example of the present embodiment, the manufacture of the bathwater is a method for manufacturing a medium.

The bathwater will be described in more detail. Tap water is typically stored as the bathwater in a general bathtub (including a bathtub in a public bathhouse, a public bathtub, and an interior or exterior bathtub set up by a Japanese inn). Before or after the storage of the bathwater, by performing a contact step of disposing or charging the above-described composite composition into the bathtub to bring the composite composition into contact with bathwater as the medium, hydrogen ($H_2$) is generated. Therefore, as it were, the composite composition of the present embodiment can be employed as a bath additive.

Therefore, the hydrogen ($H_2$) produced by the above-described contact step can be brought into contact with the bathing human skin and/or mucous membrane through the bath water as the physiologically acceptable medium. As a result, the present embodiment makes it possible to take hydrogen ($H_2$) in the human body (including the skin itself or the mucous membrane itself) using means different from that of the oral intake.

Other Embodiment (3)

For example, other aspect which can be employed is also a layer shaped body formed by layering the composite composition of each of the above-described embodiments or modified examples thereof, or a layer shaped body containing the composite composition in abase material formed in a layered form. Therefore, the layer shaped body can exhibit a function as a hydrogen supply material.

In the present embodiment, by using the layer shaped body formed by layering the composite composition, or the layer shaped body containing the composite composition in the base material formed in the layered form, a laminated structure 100 of the layer shaped body and the medium can be formed. FIG. 8(a) is a side view showing a laminated structure 100 of a layer shaped body and a medium before hydrogen is generated, and FIG. 8(b) is a side view showing the laminated structure 100 of the layer shaped body and the medium when hydrogen is generated.

As shown in FIGS. 8(a) and 8(b), the above-described laminated structure 100 includes at least a layer shaped body 10a and a medium 90b on or above a base part 20 (e.g., a fiber, a natural resin, a synthetic resin, a metal, a semiconductor, ceramics, or glass). Here, a suitable example of the medium 90b is a material which is physiologically acceptable and is at least one selected from the group consisting of a liquid form, a gel form, a cream form, a paste form, an emulsion form, and a mousse form. The medium 90b can contain a pH adjusting agent typified by sodium hydrogen carbonate. As one suitable aspect, the base part 20 has elasticity. The base part 20 is not necessarily provided when the laminated structure 100 of the layer shaped body 10a and the medium 90b can be held without particularly providing the base part 20.

As shown in FIG. 8(a), in a stage before generation of hydrogen, a film 70 which is impermeable to water is provided between the layer shaped body 10a and the medium 90b so as not to allow the layer shaped body 10a to be brought into contact with the medium 90b. A membrane formed of a known impermeable material can be utilized as the film 70. For example, an example of the material for the film 70 which is impermeable to water is a polymer such as known polyethylene. As another example, one aspect which can be employed is also use of a water-disintegrable and impermeable sheet disclosed in International Publication No. WO 2011/036992.

Meanwhile, as shown in FIG. 8(b), drawing the film 70 in the arrow direction at least partially brings the layer shaped body 10a into direct contact with the medium 90b. As a result, the layer shaped body 10a can be brought into contact with the medium 90b capable of containing a water-containing liquid having a. pH value of 7 or more (more suitably more than 7, and still more suitably more than 7.4) to generate hydrogen in cooperation with the pH adjusting agent typified by sodium hydrogen carbonate.

The present embodiment forms the structure so that drawing the film 70 in the arrow direction (toward the left on the paper) brings the layer shaped body 10a into direct contact with the medium 90b, but the method for removing the film 70 is not particularly limited. For example, one aspect which can be employed is formation of the structure so that the medium 90b is brought into contact with the composite composition (the layer shaped body 10a in the present embodiment) when the film 70 is at least partially removed or dissolved. As regards an example of the material for at least partially dissolving the film 70, one aspect which can be employed is also employment of a water-disintegrable and impermeable sheet disclosed in International Publication No. WO 2011/036992.

Another aspect which can be employed is also covering of the composite composition of each of the above-described embodiments or modified examples thereof with the film 70 which is impermeable to water in place of the layer shaped body 10a in a stage before generation of hydrogen. When removal or dissolution of the film 70 at least partially brings the composite composition into direct contact with the medium 90b, the same effects as those of the layer shaped body 10a can be exhibited.

When the medium is, for example, at least one selected from the group consisting of a liquid form, a gel form, a cream form, a paste form, an emulsion form, and a mousse form, the two layers (the layer shaped body 10a and the medium 90b) shown in FIG. 8(b) are considered not to possibly retain a state of being clearly separated from each other. Such a case increases the contact area between the layer shaped body 10a and the medium 90b, and is thus preferred from the viewpoint of more accurately promoting the generation of hydrogen. One aspect which can be employed is also the medium containing a physiologically acceptable adhesive in order to adhere to the human body site, for example.

Modified Example of Other Embodiment (3)

As one modified example of the above-described other embodiment (3), a layer shaped body formed by layering the composite composition can also be employed as a single body or as a laminated structure with a base part 20. A structure 200 as one example shown in FIG. 9 includes a layer shaped body 10a on the base part 20. The base part 20 is not necessarily provided when the shape of the layer shaped body can be held without providing the base part 20. A film 70 which is impermeable to water may be provided so as to cover the layer shaped body 10a, from the viewpoint of accurately avoiding contact with moisture in the air.

As shown in FIG. 9, for example, as one suitable aspect of the present embodiment, hydrogen is generated by bringing the layer shaped body 10a into contact with the human skin or mucous membrane and then bringing the layer shaped body 10a into contact with moisture-containing sweat or body fluid from the skin or mucous membrane. Such an aspect also allows a human to take hydrogen in his body in the same manner as in the other embodiment (3). It is also possible to supply, as the moisture, water (clean water or the like) in place of the sweat or the body fluid by, for example, spraying before (e.g., directly before) using the layer shaped body 10a.

It is particularly worth mentioning that the structures or laminated structures which can be employed in the other embodiment (3) and modified example thereof are structures which can be employed in various "life scenes". For example, typical commercial product examples which can employ (may include) the medium are the following items (A) to (D):
- (A) one washing agent selected from the group consisting of face-wash, hair shampoo, body shampoo, liquid hand soap, and liquid body soap;
- (B) one cosmetic material selected from the group consisting of beauty lotion (e.g., one containing hyaluronic acid), beauty essence, emulsion, lotion, beauty cream (e.g., one containing collagen), foundation, a skin pack (including a skin pack containing gel (or a gel agent)), shaving cream, hair rinse, hair treatment, a hair conditioner, a hair cosmetic, a diaphoretic, and a cosmetic substance for UV protection;
- (C) one therapeutic material selected from the group consisting of ointment and fomentation; and
- (D) one hygienic material selected from the group consisting of a water-absorbent resin, water-absorbent nonwoven fabric, water-absorbent fiber, water-absorbent felt, and water-absorbent gel (or gelled agent).

Here, the above-described "hair cosmetic" includes hair dressing, hair oil, camellia oil, styling (material), setting (material), blowing (material), brushing (material), tic, hair stick, hair wax, hair foam, hair gel, pomade, hair cream, hair solid, hair lacquer, hair liquid, hair spray, and hair water. The above-described "hygienic material" includes a hygienic glove, a head cover, a head band, a bed pad, a bed sheet, an incontinence article for adults, a sanitary product, a clothing item, a wound treatment product (including a wound covering material, tape, and a bandage), a disposable diaper including a diaper for adults and a diaper for infants, gauze, a gown, a hygienic tissue (including a wet towel, a face washing towel, a patch, a wet tissue, and a napkin), absorbent cotton, a cotton swab, adhesive-plaster, and surgical tape.

Other Embodiment (4)

The composite composition of each of the above-described embodiments or modified examples thereof can also be used as foods for a rearing (in the present application, including feeding on a pasture) animal (including dog, cat, horse, sheep, rabbit or chicken, and excluding fish), a food animal, an animal (including fox, bear, deer, snake, or crocodile) whose hair or skin can be used for clothing or leather products (including pouches, various cases or bags) or the like, an animal utilized for medical use, or a fish including a fish for aquaculture, or the like. Furthermore, the composite composition can also be used as an industrial medicine or agent.

The composite composition of each of the above-described embodiments or modified examples thereof can be utilized as a human supplement or a food additive. In the meantime, it is particularly worth mentioning that the composite composition of each of the above-described embodiments or modified examples thereof has a hydrogen generating capability, whereby the composite composition can exhibit an antiseptic function for various foods or materials. For example, fresh foods including vegetables, fruits, fresh fishes, and meats are brought into contact with the composite composition containing water, or water in which the composite composition is immersed, whereby the lives of the fresh foods can be increased. By immersing the composite composition in various cosmetics or perfumery including perfume, emulsion, or beauty lotion which contains water (moisture), the lives of the cosmetics or perfumery can be increased.

Other Embodiment (5)

The composite composition of each of the above-described embodiments or modified examples thereof can aggregate in a natural state to form aggregates having a diameter size at urn level (e.g. about 20 μm). A compound can be formed as a lump solid preparation which is obtained by the aggregates or artificially assembling the composite composition through addition of a binding agent, compression, or the like and has such a size to be picked up by human fingers. The compound may also be applied to plants (including trees).

Specifically, in the present embodiment, the compound is buried in soil (containing moisture) in which the plant is planted or naturally grown, to utilize the soil as the medium containing the water-containing liquid. The compound is brought into contact with the soil as the medium to generate hydrogen ($H_2$). As a result, it is possible for the plant brought into contact with the soil to take hydrogen in its body through its root, stem, or cortex. As a result, it is possible to realize prevention or suppression of photosynthesis inhibition, leaf discoloration, growth promotion, and/or withering of a plant. Some plants are also capable of realizing an increase in sugar content. A typical example of the moisture in the present embodiment is rainwater or artificial water. The number or the amount of the compound in the soil is not particularly limited.

Another aspect of the present embodiment which can be employed is also introducing or charging the compound into a naturally present or artificial puddle (medium) to bring the compound into contact with the water-containing liquid. The compound is brought into contact with the water-containing liquid to generate hydrogen ($H_2$). In this aspect, an animal is brought into contact with or immersed in the above-described puddle to be capable of taking hydrogen in its body through the water-containing liquid. As a result, the hydrogen directly, or dermally or transmucosally taken in the body is capable of appropriately eliminating, removing, or reducing excess active oxygen (particularly hydroxyl radicals) in the body of the animal, whereby the health promotion and/or disease prevention of the animal can be realized.

If the above-described puddle has a pH value higher than weak acidity (e.g., a pH value of 5 or more), the use a mixture of the compound of the present embodiment and sodium hydrogen carbonate provides a high pH value, which can satisfy the condition as the medium allowing easy generation of hydrogen ($H_2$). In other words, when the water-containing liquid such as a puddle is acidic, a large amount of compound is required to be introduced or charged into the soil in order to satisfy the condition as the medium allowing easy generation of hydrogen ($H_2$).

The mixture of the compound of the present embodiment and sodium hydrogen carbonate is used, whereby, even if the soil or the puddle as the medium is neutral or weakly acidic, the compound is buried, introduced, or charged into the soil or the puddle as the medium to undergo a contact step of bringing the composite composition into contact with the medium. As a result, the generation of hydrogen ($H_2$) can be promoted.

Therefore, it is possible to bring hydrogen ($H_2$) produced by the above-described contact step into contact with the skin and/or the mucous membrane of an animal or with the leaf, stem, cortex, and/or root of a plant through the soil or the puddle as the medium. As a result, the present embodiment allows an animal or a plant to take hydrogen ($H_2$) in its body. For example, the hydrogen can exhibit a function of suppressing the aging of the animal. The hydrogen can exhibit a function of suppressing the corrosion of the plant.

The present embodiment is not limited to the case where the composite composition or the compound is used as it is. One suitable aspect which can be employed is also an aspect in which the complex composition or the compound is contained in a "base material" such as a pharmaceutical product for an animal, a livestock or pet food, a food for rearing of an animal, a pharmaceutical product for a plant, a fertilizer for a plant, or a compost for a plant, or an aspect in which the complex composition or the compound is blended in the "base material". For example, as a typical example, 0.1% by weight to 50% by weight of the composite composition or the compound is mixed or kneaded as an additive in the base material. Therefore, in the present embodiment, not only the compound obtained by blending the composite composition with a pharmaceutical product for a plant, a fertilizer for a plant, or a compost for a plant, but also the above-described "base material" mean a "compound" in a broad sense. Therefore, for example, one suitable means which can be employed in order that an animal or a plant dermally or transmucosally takes hydrogen in the body is bringing the above-described base material into contact with the medium.

EXAMPLES

Hereinafter, in order to describe each of the above-described embodiments in more detail, Examples will be described, but the above-described embodiments are not limited to these examples.

Example 1-1

First, 200 g of silicon fine particles having a silicon suboxide of the first embodiment (that is, one example of the composite composition of the first embodiment) was used as a raw material, and placed in a reaction vessel. 500 ml of hydrogen peroxide water having a concentration of 3% by weight was added thereto. The temperature of the reaction vessel is set to 35° C. with stirring, and the silicon fine particles are immersed in the hydrogen peroxide water for 30 minutes to perform a step of reforming the surface of the silicon fine particle. Then, the surface-reformed silicon fine particles (that is, one example of the composite composition of the modified example (1) of the first embodiment) were subjected to solid-liquid separation by vacuum filtration using ashless quantitative filter paper (manufactured by GE Healthcare Japan Corporation, grade 42, particle retention capability: 2.5 μm). Then, the silicon fine particles were washed with water, dispersed in ethanol, and then subjected to solid-liquid separation by centrifugation. The surface-reformed silicon fine particles subjected to solid-liquid separation are dried at 40° C. under reduced pressure. Then, the dried silicon fine particles are stored in a vacuum vessel, or a vessel subjected to nitrogen substitution. The surface of the silicon fine particle subjected to the reforming step exhibited hydrophilicity.

Example 1-2

First, 200 g of silicon fine particles of the first embodiment (that is, one example of the composite composition of the first embodiment) was used as a raw material, and placed in a reaction vessel. 250 ml of hydrogen peroxide water having a concentration of 10% by weight was added thereto. The temperature of the reaction vessel is set to 20° C. with stirring, and the silicon fine particles are immersed in the hydrogen peroxide water for 60 minutes to perform a step of reforming the surface of the silicon fine particle. Then, the surface-reformed silicon fine particles (that is, one example of the composite composition of the modified example (1) of the first embodiment) were subjected to solid-liquid separation by vacuum filtration using ashless quantitative filter paper (manufactured by GE Healthcare Japan Corporation, grade 42, particle retention capability: 2.5 μm). Then, the silicon fine particles were washed with water, dispersed in ethanol, and then subjected to solid-liquid separation by centrifugation. The surface-reformed silicon fine particles subjected to solid-liquid separation are dried at 40° C. under reduced pressure. Then, the dried silicon fine particles are stored in a vacuum vessel, or a vessel subjected to nitrogen substitution. The surface of the silicon fine particle subjected to the reforming step exhibited hydrophilicity.

Example 1-3

First, 200 g of silicon fine particles of the first embodiment (that is, one example of the composite composition of the first embodiment) was used as a raw material, and placed in a reaction vessel. 500 ml of hydrogen peroxide water having a concentration of 3% by weight was added thereto.

The temperature of the reaction vessel is set to 60° C. with stirring, and the silicon fine particles are immersed in the hydrogen peroxide water for 30 minutes to perform a step of reforming the surfaces of the silicon fine particles. Then, the surface-reformed silicon fine particles (that is, one example of the composite composition of the modified example (1) of the first embodiment) were subjected to solid-liquid separation by vacuum filtration using ashless quantitative filter paper (manufactured by GE Healthcare Japan Corporation, grade 42, particle retention capability: 2.5 µm). Then, the silicon fine particles were washed with water, dispersed in ethanol, and then subjected to solid-liquid separation by centrifugation. The surface-reformed silicon fine particles subjected to solid-liquid separation are dried at 40° C. under reduced pressure. Then, the dried silicon fine particles are stored in a vacuum vessel, or a vessel subjected to nitrogen substitution. The surface of the silicon fine particle subjected to the reforming step exhibited hydrophilicity.

Example 2

5 mg of silicon fine particles of first embodiment (that is, one example of the composite composition of the first embodiment) were used as a raw material. 78 ml of water having a pH of 7 and a temperature of 36° C. was added to the raw material (silicon fine particles) to disperse the raw material, and hydrogen gas generated with stirring was measured with a hydrogen concentration meter. The amount of the hydrogen gas sequentially generated is shown in Table 1. The amount of the hydrogen gas generated was also identified and quantitatively evaluated by gas chromatography-mass spectrometry (GC/MS).

After the reaction between the raw material and water was completed, the silicon fine particles after the reaction were analyzed by the XPS apparatus and the FT-JR apparatus of the first embodiment. As a result, it was shown that the silicon fine particles after the reaction still retain a hydrogen generating capability.

TABLE 1

| Elapsed time (hr) | Cumulative total hydrogen gas generation amount (ml/g) |
| --- | --- |
| 1 | 1.0 |
| 2 | 2.8 |
| 4 | 4.0 |
| 6 | 4.9 |
| 24 | 7.0 |

Example 3

5 mg of silicon fine particles (that is, surface-reformed silicon fine particles) of the modified example (1) of the first embodiment were used as a raw material. 78 ml of water having a pH of 7 and a temperature of 36° C. was added to the raw material (silicon fine particles) to disperse the raw material, and generated hydrogen gas was measured with a hydrogen concentration meter. As shown in Table 2, the amount of hydrogen gas sequentially generated was 10 times or more of that of the result of Table 1. The amount of hydrogen gas generated was also identified and quantitatively evaluated by GC/MS.

After the reaction between the raw material and water was completed, the silicon fine particles after the reaction were analyzed by the XPS apparatus and the FT-IR apparatus of the first embodiment. As a result, it was shown that the silicon fine particles after the reaction (that is, the surface-reformed silicon fine particles) still retain a hydrogen generating capability.

TABLE 2

| Elapsed time (hr) | Cumulative total hydrogen gas generation amount (ml/g) |
| --- | --- |
| 1 | 18 |
| 2 | 29 |
| 4 | 52 |
| 6 | 61 |
| 24 | 79 |

Example 4

5 mg of silicon fine particles of first embodiment (that is, one example of the composite composition of the first embodiment) were used as a raw material. 78 ml of water (aqueous solution) having a pH adjusted to 8.3 and a temperature of 36° C. using sodium hydrogen carbonate was added to the raw material (silicon fine particles) to disperse the raw material, and generated hydrogen gas was measured with a hydrogen concentration meter. The amount of the hydrogen gas sequentially generated is shown in Table 3. The amount of the hydrogen gas generated was also identified and quantitatively evaluated by GC/MS.

After the reaction between the raw material and water was completed, the silicon fine particles after the reaction were analyzed by the XPS apparatus and the FT-IR apparatus of the first embodiment. As a result, it was shown that the silicon fine particles after the reaction still retain a hydrogen generating capability.

TABLE 3

| Elapsed time (hr) | Cumulative total hydrogen gas generation amount (ml/g) |
| --- | --- |
| 1 | 3 |
| 2 | 6 |
| 4 | 13 |
| 6 | 20 |
| 10 | 32 |

Example 5

5 mg of silicon fine particles (that is, surface-reformed silicon fine particles) of the modified example (1) of the first embodiment were used as a raw material. 78 ml of water (aqueous solution) having a pH of 8.3 and a temperature of 36° C. using sodium hydrogen carbonate was added to the raw material (silicon fine particles) to disperse the raw material, and generated hydrogen gas was measured with a hydrogen concentration meter. As shown in Table 4, the amount of the hydrogen gas sequentially generated was 15 times or more of that of the result of Table 3. The increase in the hydrogen generation amount is an effect due to the pH vale becoming alkaline. More characteristically, compared with the results in Table 3, the amount of the hydrogen gas generated, particularly in the initial stage of the reaction, significantly increased. The amount of the hydrogen gas generated was also identified and quantitatively evaluated by GC/MS.

After the reaction between the raw material and water was completed, the silicon fine particles after the reaction were analyzed by the XPS apparatus and the FT-IR apparatus of the first embodiment. As a result, it was shown that the silicon fine particles after the reaction (that is, the surface-reformed silicon fine particles) still retain a hydrogen generating capability.

TABLE 4

| Elapsed time (hr) | Cumulative total hydrogen gas generation amount (ml/g) |
| --- | --- |
| 1 | 72 |
| 2 | 120 |
| 4 | 216 |
| 12 | 368 |
| 20 | 398 |

Example 6

200 g of silicon fine particles of the first embodiment (that is, one example of the composite composition of the first embodiment) was used as a raw material. To the raw material (silicon fine particles), 250 ml of hydrogen peroxide water obtained by diluting 35% hydrogen peroxide and having a concentration of 10% by weight was added to disperse the raw material. Under the condition of 35° C., the silicon fine particles are immersed in the hydrogen peroxide water for 30 minutes to perform a reforming step of reforming the surfaces of the silicon fine particles. Then, the surface-reformed silicon fine particles (that is, one example of the composite composition of the modified example (1) of the first embodiment) were subjected to solid-liquid separation by vacuum filtration using ashless quantitative filter paper (manufactured by GE Healthcare Japan Corporation, grade 42, particle retention capability: 2.5 μm). The silicon fine particles were dispersed in ethanol, and then subjected to solid-liquid separation by centrifugation. The surface-reformed silicon fine particles subjected to solid-liquid separation are dried at 40° C. under reduced pressure. Then, the dried silicon fine particles are stored in a vacuum vessel, or a vessel subjected to nitrogen substitution. The surface of the silicon fine particle subjected to the reforming step exhibited hydrophilicity.

Then, as a result of analyzing the surfaces of the silicon fine particles using an XPS analyzer, the number of silicon atoms in the silicon oxide membrane (that is, the ratio of the number of silicon atoms in a silicon suboxide to the total of the number of silicon atoms of silicon dioxide and the number of silicon atoms of the silicon suboxide (100%)) (that is, the composition ratio of the silicon suboxide) was about 60%.

Example 7

An example in which sodium percarbonate is employed in place of hydrogen peroxide water of the modified example (1) of the first embodiment will be described.

5 mg of silicon fine particles of first embodiment (that is, one example of the composite composition of the first embodiment) were used as a raw material. 180 ml of water was added to the raw material (silicon fine particles), and 1.8 g of sodium percarbonate was further added thereto, to prepare an aqueous solution, and the raw material was dispersed in the aqueous solution. Under the condition of 30° C., the silicon fine particles are immersed with stirring for 30 minutes to perform a reforming step of reforming the surfaces of the silicon fine particles. Then, the surface-reformed silicon fine particles (that is, one example of the composite composition of the modified example (1) of the first embodiment) were subjected to solid-liquid separation by vacuum filtration using ashless quantitative filter paper (manufactured by GE Healthcare Japan Corporation, grade 42, particle retention capability: 2.5 μm). Then, sodium carbonate adhering to the silicon fine particles was removed by washing with water, and the silicon fine particles were then dispersed in ethanol, followed by solid-liquid separation by centrifugation. The surface-reformed silicon fine particles subjected to solid-liquid separation are dried at 40° C. under reduced pressure. Then, the dried silicon fine particles are stored in a vessel subjected to nitrogen substitution. The surface of the silicon fine particle subjected to the reforming step exhibited hydrophilicity.

Example 8

5 mg of silicon fine particles (that is, silicon fine particles surface-reformed with sodium percarbonate) obtained in Example (7) were used as a raw material. 78 ml of water having a pH of 7 and a temperature of 36° C. was added to the raw material (silicon fine particles) to disperse the raw material in the water. In this example, the amount of hydrogen gas generated by immersing the raw material in the aqueous solution was measured using a hydrogen concentration meter.

The membrane thickness of the silicon oxide membrane (including silicon dioxide and a silicon suboxide) after the elapse of 168 hours (7 days) from the time of hydrogen generation was confirmed to be about 13 nm. Therefore, if the membrane thickness of the silicon oxide membrane after the elapse of 168 hours (7 days) from the time of hydrogen generation is within the numerical range of 3 nm or more and 20 nm or less (typically 15 nm or less) as already described, the silicon fine particles of the modified example (1) of the first embodiment can be accurately recognized.

Example 9

5 mg of silicon fine particles of first embodiment (that is, one example of the composite composition of the first embodiment) were used as a raw material. 78 ml of water (aqueous solution) having a pH adjusted to 10 and a temperature of 36° C. using sodium hydrogen carbonate and sodium carbonate was added to the raw material (silicon fine particles) to prepare an aqueous solution, and the raw material was dispersed in the aqueous solution. In this example, the amount of hydrogen gas generated by immersing the raw material in the aqueous solution was measured using a hydrogen concentration meter. The amount of hydrogen sequentially generated significantly increased compared with the case of using water having a pH of 7 or 8.3. The amount of the hydrogen generated was also identified and quantitatively evaluated by GC/MS. FIG. 5 is a graph showing the relationship between the amount of the hydrogen gas generated and a reaction time in this example.

Example 10

5 mg of silicon fine particles of first embodiment (that is, one example of the composite composition of the first embodiment) were used as a raw material. 78 ml of water (aqueous solution) having a pH adjusted to 8.3 and a temperature of 36° C. using caustic soda was added to the raw material (silicon fine particles) to prepare an aqueous solution, and the raw material was dispersed in the aqueous solution. In this example, the amount of hydrogen gas generated by immersing the raw material in the aqueous solution was measured using a hydrogen concentration meter. The amount of hydrogen sequentially generated significantly increased compared with the case of using water having a pH of 7. The amount of the hydrogen generated was also identified and quantitatively evaluated by GC/MS.

Example 1

5 mg of silicon fine particles (that is, surface-reformed silicon fine particles) of the modified example (1) of the first embodiment were used as a raw material. 30 ml of water (aqueous solution) having a pH adjusted to 8.3 and a temperature of 36.5° C. using caustic soda was produced, and added to the raw material (silicon fine particles) to disperse the raw material in the aqueous solution. In this example, the amount of hydrogen gas generated by immersing the raw material in the aqueous solution was measured using a hydrogen concentration meter. The amount of hydrogen sequentially generated significantly increased compared with the case of using water having a pH of 7. The amount of the hydrogen generated was also identified and quantitatively evaluated by GC/MAS.

Example 12

5 mg of silicon fine particles of first embodiment (that is, one example of the composite composition of the first embodiment) were used as a raw material. 78 ml of water (aqueous solution) having a pH adjusted to 8.3 and previously heated to 60° C. using caustic soda was added little by little to the raw material (silicon fine particles) to disperse the raw material in the aqueous solution. In this example, the amount of hydrogen gas generated by immersing the raw material in the aqueous solution was measured using a hydrogen concentration meter.

In this example, hydrogen was confirmed to be significantly rapidly generated compared with the results shown in Table 3, for example. The generation rate of the hydrogen sequentially generated significantly increased compared with the case of using water having a pH of 7. The amount of the hydrogen generated was also identified and quantitatively evaluated by GC/MS.

Example 13

5 mg of silicon fine particles (that is, surface-reformed silicon fine particles) of the modified example (1) of the first embodiment were used as a raw material 78 ml of water (aqueous solution) having a pH adjusted to 10 and previously heated to 60° C. using caustic soda was added little by little to the raw material (silicon fine particles) to disperse the raw material in the aqueous solution. In this example, the amount of hydrogen gas generated by immersing the raw material in the aqueous solution was measured using a hydrogen concentration meter.

In this example, hydrogen was confirmed to be more rapidly generated compared with the case of Example 11. The amount of the hydrogen generated was also identified and quantitatively evaluated by GC/MS.

Example 14

A composite composition manufactured in the second embodiment was subjected to solid-liquid separation by vacuum filtration using ashless quantitative filter paper (manufactured by GE Healthcare Japan Corporation, grade 42, particle retention capability: 2.5 μm). The surface-reformed silicon fine particles subjected to solid-liquid separation are dried at 40° C. under reduced pressure. Then, the dried silicon fine particles are stored in a vacuum vessel, or a vessel subjected to nitrogen substitution. The surface of the composite composition manufactured in the second embodiment exhibited hydrophilicity.

One example of the composite composition obtained in Example 14 is mainly composed of silicon nanopowder having a crystallite diameter of 1 nm or more and 500 nm or less. More specifically, the silicon nanopowder were measured by an X-ray diffractometer (Smart Lab, manufactured by Rigaku Corporation), and as a result, as one example, the average crystallite diameter of the silicon nanopowder was 28.0 nm. The above-described result of the average crystallite diameter is merely a result of the pulverizing step and the like as one example, and therefore the present Example is not limited to the above-described numerical values.

Example 15

5 mg of silicon fine particles (that is, one example of the composite composition of the second embodiment) obtained in Example 14 was used as a raw material. 78 ml of water having a pH of 7 and a temperature of 36° C. was added to the raw material (silicon fine particles) to disperse the raw material, and hydrogen gas generated with stirring was measured with a hydrogen concentration meter. The amount of the hydrogen gas sequentially generated is shown in Table 5. The amount of the hydrogen gas generated was also identified and quantitatively evaluated by gas chromatography-mass spectrometry (GC/MS).

TABLE 5

| Elapsed time (hr) | Cumulative total hydrogen gas generation amount (ml/g) |
| --- | --- |
| 1 | 22 |
| 2 | 41 |
| 4 | 78 |
| 6 | 108 |
| 24 | 220 |

In the meantime, the silicon fine particles of each of the above-described embodiments can be brought into contact with a first water-containing liquid having a pH value of less than 7 in a first contact step, and then brought into contact with a second water-containing liquid having a pH value of 7 or more in a second contact step to generate hydrogen in the second contact step. Therefore, the silicon fine particles of each of the above-described embodiments can have a remarkable hydrogen generating capability when brought into contact with a water-containing liquid having a pH value of 7 or more.

The temperature condition of the second water-containing liquid for generation of hydrogen in each of the above-described embodiments is not limited. The temperature of the second water-containing liquid may depend on the pH of the second water-containing liquid, but if the temperature is 80° C. or lower, the generation of the hydrogen is accurately promoted. However, the upper limit of the temperature of the second water-containing liquid is not essentially limited. For example, when the composite composition of the present embodiment is used as an industrial medicine, the temperature may exceed 50° C. However, as the temperature is higher, there are problems that the equipment (including a vessel) is required to have higher heat resistance, and the care is required for handling. Therefore, the composite composition is preferably used at a temperature of 100° C. or lower even when the composite composition is used as an industrial medicine.

INDUSTRIAL APPLICABILITY

The composite composition of the present invention can be widely utilized in various industries including hydrogen-utilizing agriculture, stock farming, forest industry, fishing industry, pet industry, industries of bonsai plants and flower arrangement, pharmaceuticals (including quasi-drugs) and medical industry, food industry, veterinary industry, tree medicine industry, industries handling industrial reducing agents, rust preventive uses, and industrial chemical synthesis processes, and new energy industries such as fuel cells.

The invention claimed is:

1. A composite composition comprising:
   a silicon fine particle having a capability of generating hydrogen; and
   a silicon suboxide ($SiO_x$, wherein x is ½, 1, or 3⁄2) and/or a mixed composition of the silicon suboxide and silicon dioxide, at least partially covering a surface of the silicon fine particle,
   wherein a concentration of a hydroxyl group on the surface of the silicon fine particle is $5 \times 10^{13}/cm^2$ or more, and
   wherein the composite is orally ingestible.

2. The composite composition according to claim 1, wherein the silicon fine particle contains silicon nanopowder.

3. The composite composition according to claim 1, wherein a composition ratio of the silicon suboxide (a ratio of number of silicon atoms) in a silicon oxide membrane which is a membrane of the mixed composition is 10% or more and 80% or less.

4. The composite composition according to claim 1, wherein a thickness of a silicon oxide membrane which is a membrane of the mixed composition is 0.5 nm or more and 15 nm or less.

5. The composite composition according to claim 1, wherein the surface of the silicon fine particle has a SiOH group, and is hydrophilic.

6. The composite composition according to claim 1, wherein a number density of a SiH group on the surface of the silicon fine particle is $2 \times 10^{14}/cm^2$ or less.

7. A pharmaceutical product comprising the composite composition according to claim 1.

8. A quasi-drug comprising the composite composition according to claim 1.

9. A hydrogen supply material comprising:
   the composite composition according to claim 1; and
   a physiologically acceptable medium brought into contact with the composite composition,
   the hydrogen supply material being adapted to bring hydrogen produced from the composite composition through the medium into contact with a skin and/or a mucous membrane.

10. The hydrogen supply material according to claim 9, further comprising a film which is impermeable to water covering the composite composition, or a layer containing the composite composition,
    wherein the medium is brought into contact with the composite composition when the film is at least partially removed or when the film is at least partially dissolved.

11. The hydrogen supply material according to claim 9, wherein the medium is at least one selected from the group consisting of a liquid, a gel, a cream, a paste, an emulsion, and a mousse.

12. A food for rearing comprising the composite composition according to claim 1.

13. The food for rearing according to claim 12 for an animal (excluding a fish).

14. The food for rearing according to claim 12 for a fish.

15. A supplement comprising the composite composition according to claim 1.

16. A food additive comprising the composite composition according to claim 1.

17. A health food comprising the composite composition according to claim 1.

18. A compound obtained by blending the composite composition according to claim 1 with a pharmaceutical product for a plant, a fertilizer for a plant, or a compost for a plant.

19. A fresh food, a cosmetic, or a perfumery, wherein the composite composition according to claim 1 and water are brought into contact with each other.

* * * * *